(12) United States Patent
Ross et al.

(10) Patent No.: US 11,793,124 B2
(45) Date of Patent: *Oct. 24, 2023

(54) SYSTEM FOR GROWING FUNGAL MATERIALS

(71) Applicant: MycoWorks, Inc., Emeryville, CA (US)

(72) Inventors: Philip Ross, San Francisco, CA (US); Nicholas Wenner, Sebastopol, CA (US); Caitlin Moorleghen, Emeryville, CA (US)

(73) Assignee: Myco Works, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/728,480

(22) Filed: Apr. 25, 2022

(65) Prior Publication Data

US 2022/0279736 A1 Sep. 8, 2022

Related U.S. Application Data

(63) Continuation of application No. 17/326,742, filed on May 21, 2021, now Pat. No. 11,310,968, which is a continuation of application No. 17/081,745, filed on Oct. 27, 2020, now Pat. No. 11,013,189, which is a continuation of application No. 15/884,788, filed on Jan. 31, 2018, now Pat. No. 10,842,089, which is a continuation of application No. 15/650,779, filed on Jul. 14, 2017, now Pat. No. 10,687,482.

(60) Provisional application No. 62/362,462, filed on Jul. 14, 2016.

(51) Int. Cl.
*A01G 18/60* (2018.01)
*A01G 18/62* (2018.01)
*C05F 9/04* (2006.01)
*C05F 11/08* (2006.01)
*A01G 18/10* (2018.01)

(52) U.S. Cl.
CPC ............. *A01G 18/62* (2018.02); *A01G 18/10* (2018.02); *A01G 18/60* (2018.02); *C05F 9/04* (2013.01); *C05F 11/08* (2013.01); *Y02A 40/20* (2018.01); *Y02P 20/145* (2015.11)

(58) Field of Classification Search
CPC ........ A01G 18/62; A01G 18/10; A01G 18/60; C05F 9/04; C05F 11/08; Y02A 40/20; Y02P 20/145; Y02P 20/582; C12N 1/14; C12N 1/02
See application file for complete search history.

(56) References Cited

U.S. PATENT DOCUMENTS

2008/0145577 A1* 6/2008 Bayer et al. ................. 428/35.6
2011/0269218 A1* 11/2011 Kalisz et al. .............. 435/254.1

* cited by examiner

*Primary Examiner* — Satyendra K Singh
(74) *Attorney, Agent, or Firm* — Temmerman Law; Mathew J. Temmerman

(57) ABSTRACT

A system for growing fungi, the system comprising a nutritive vehicle, a porous material, an administrable space, fungal tissue comprising fungal hyphae having a growth pattern, the fungal tissue connecting said nutritive vehicle to said porous material to said administrable space, wherein the fungal tissue within said space defines at least one successive fungal material layer; and a chemically or physically altered separated portion of fungal material, the separated portion separated from said fungal tissue.

6 Claims, 23 Drawing Sheets

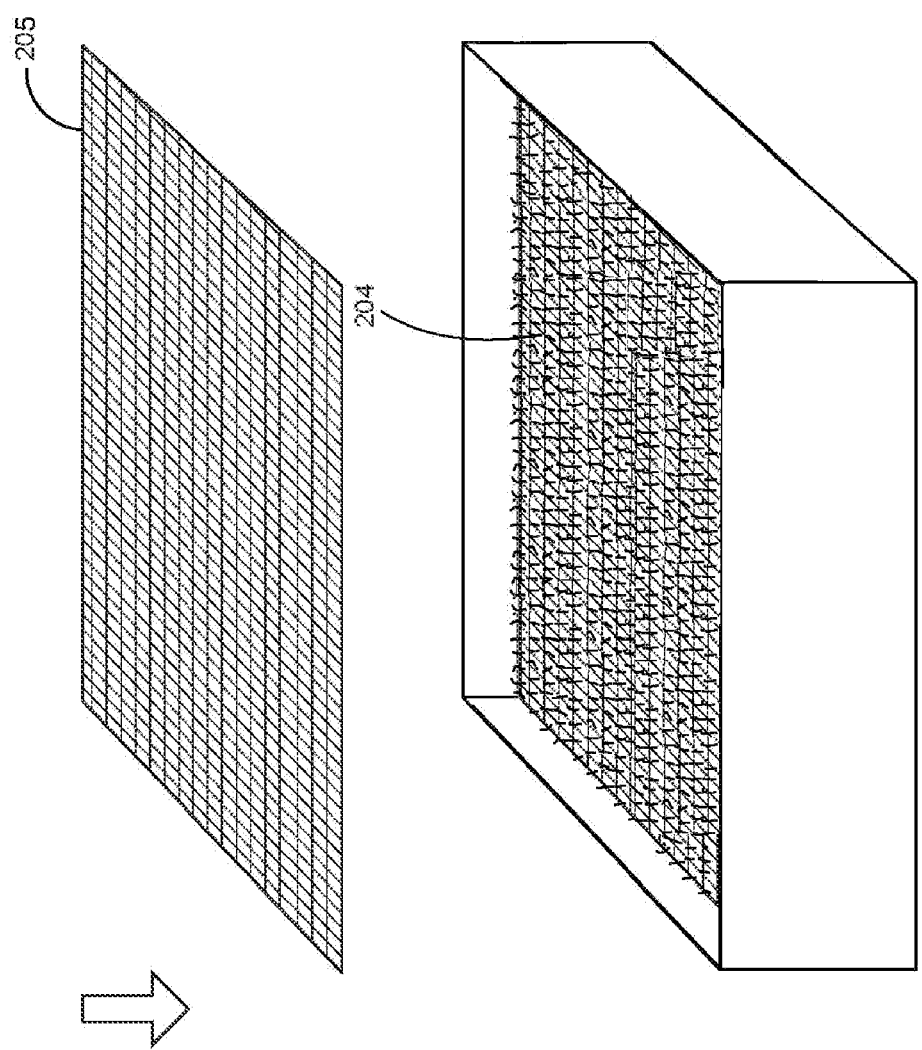

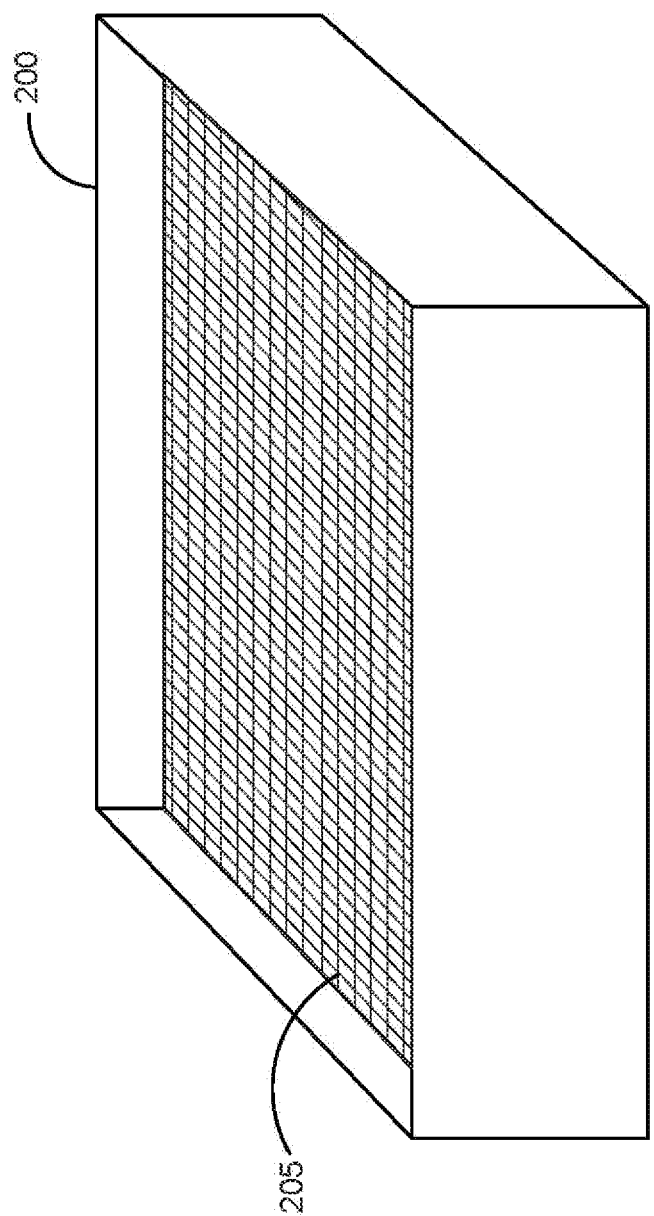

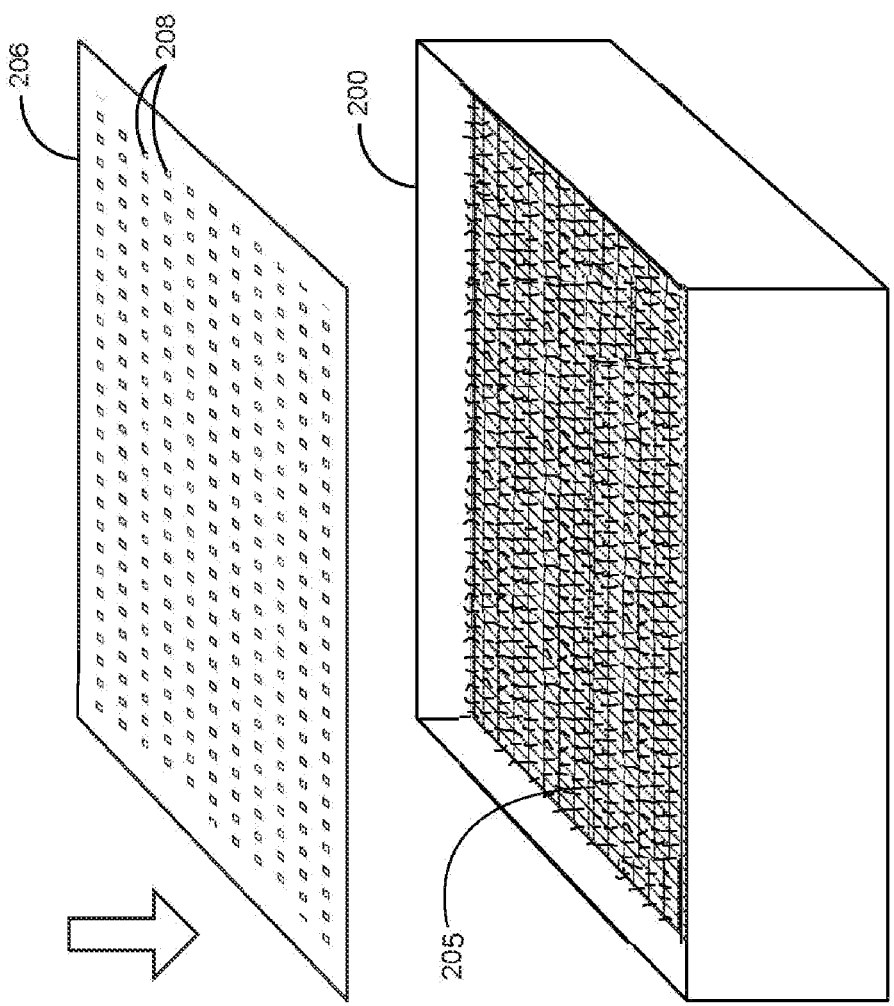

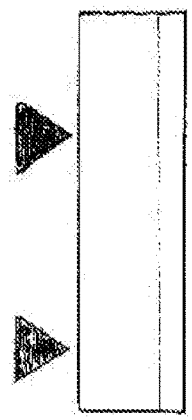
Fig. 15A
Fig. 15B
Fig. 15C
Fig. 15D
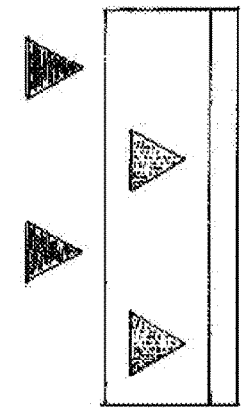
Fig. 15E
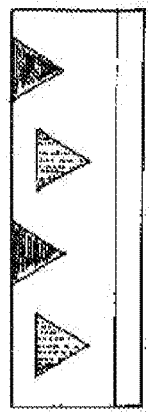
Fig. 15F
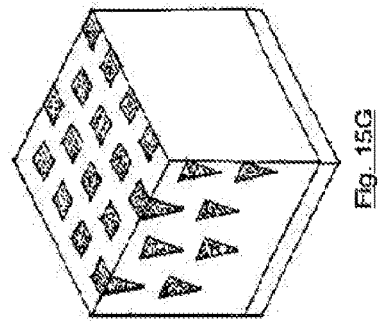
Fig. 15G

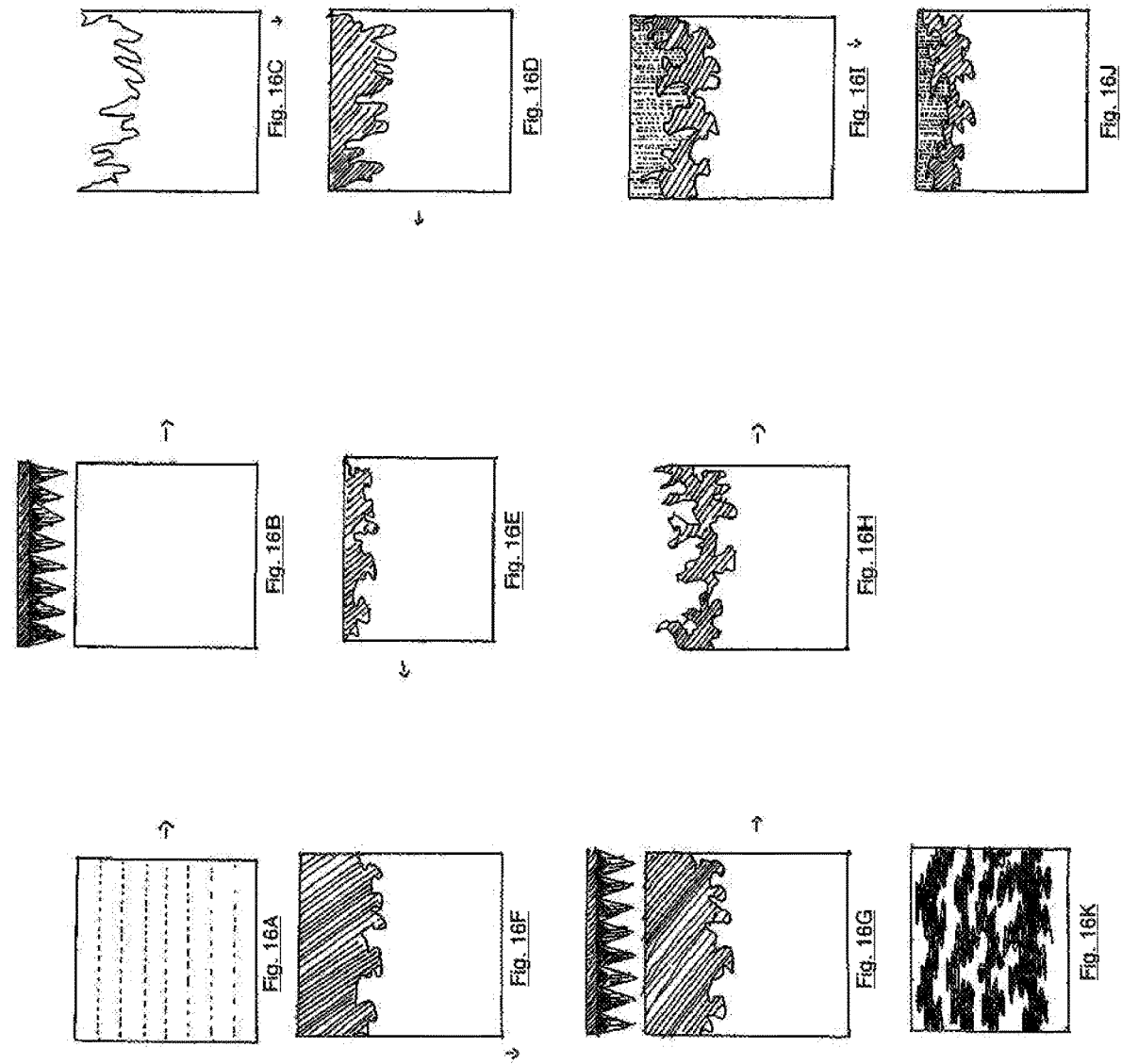

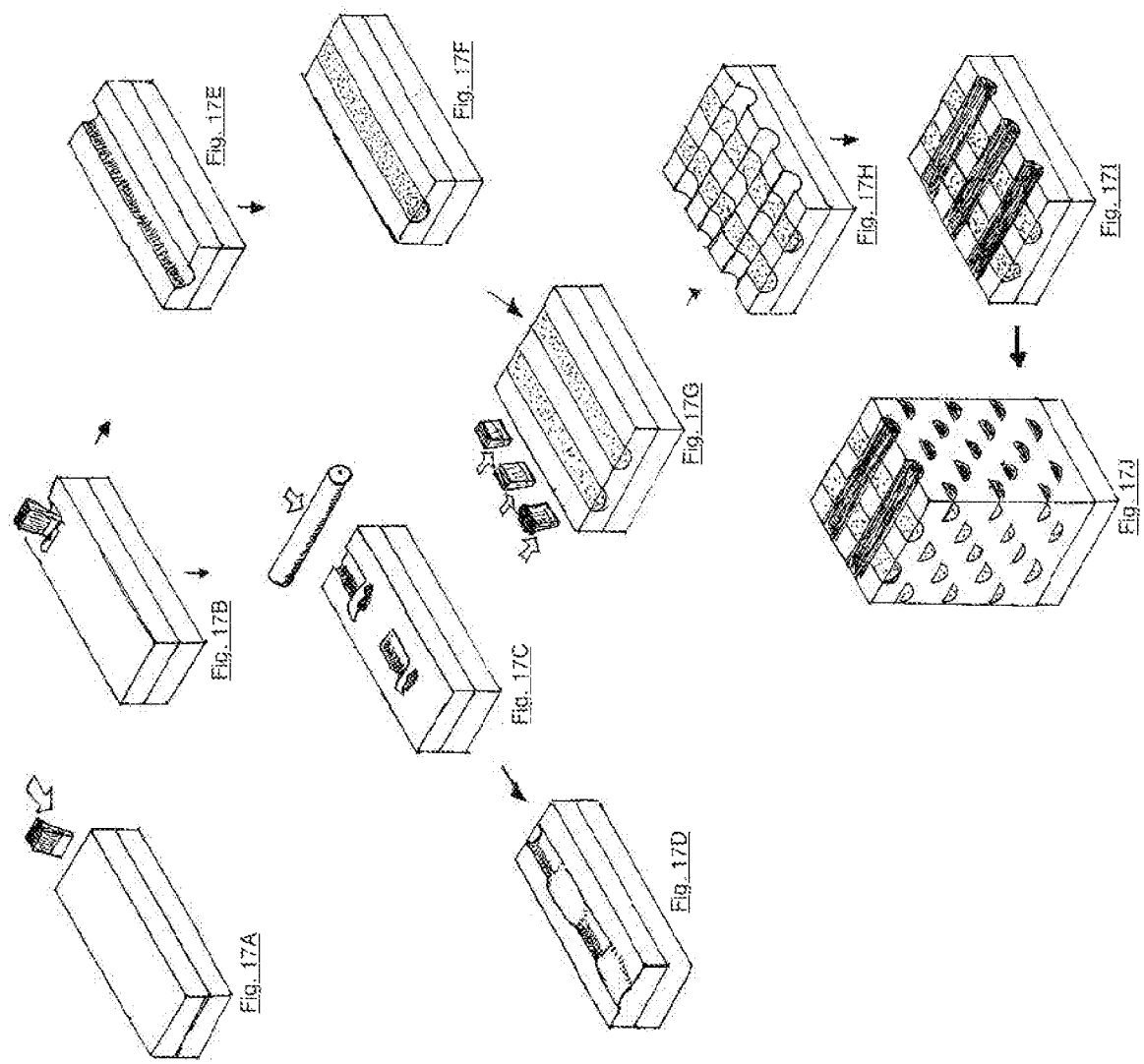

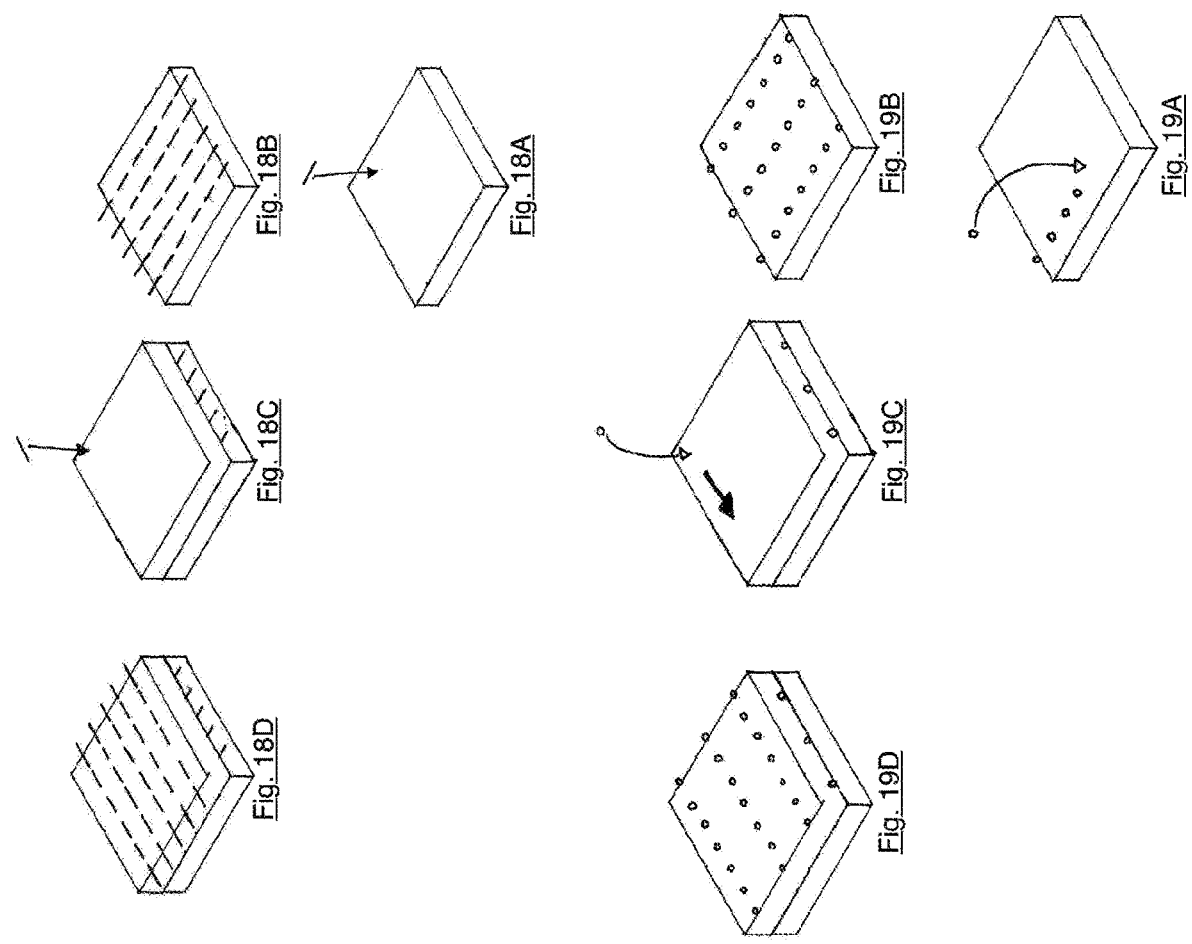

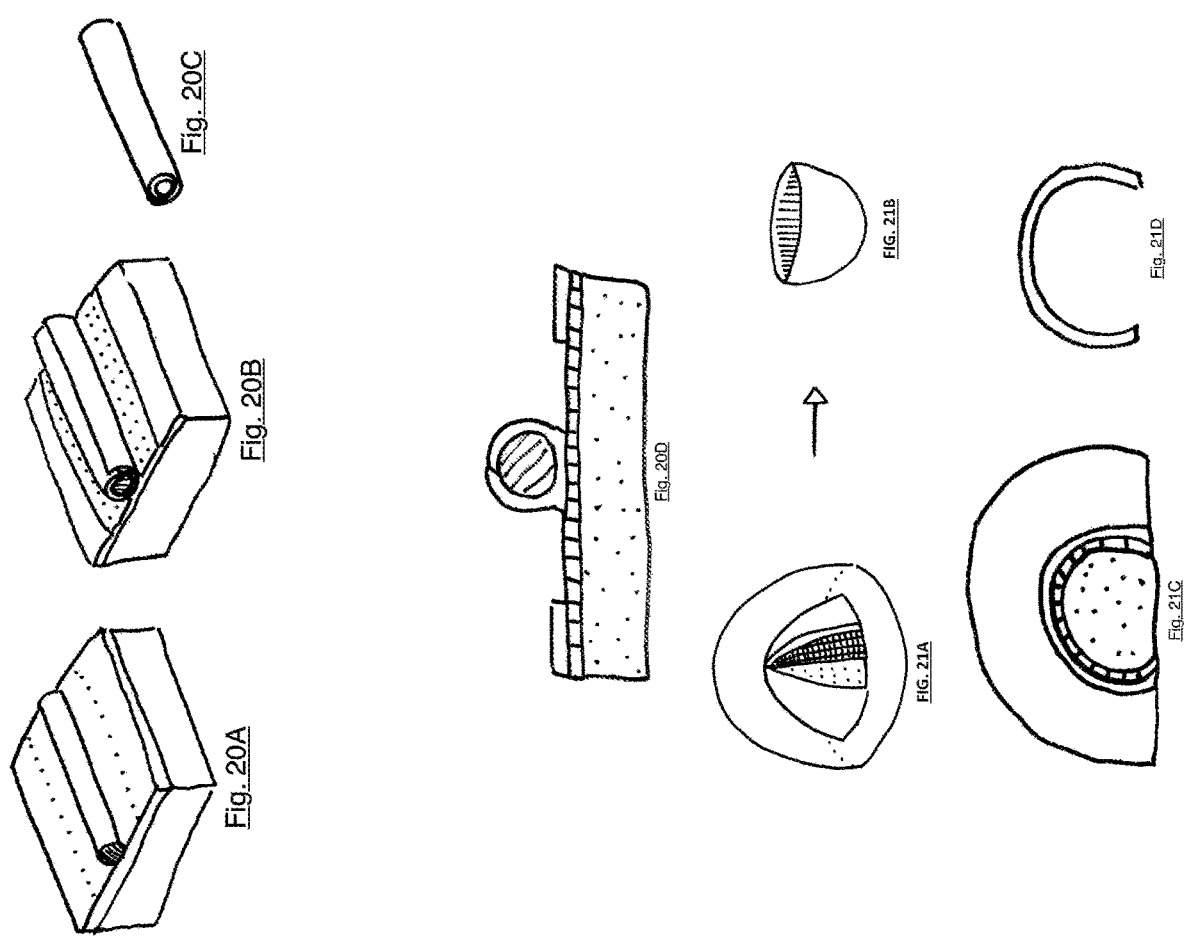

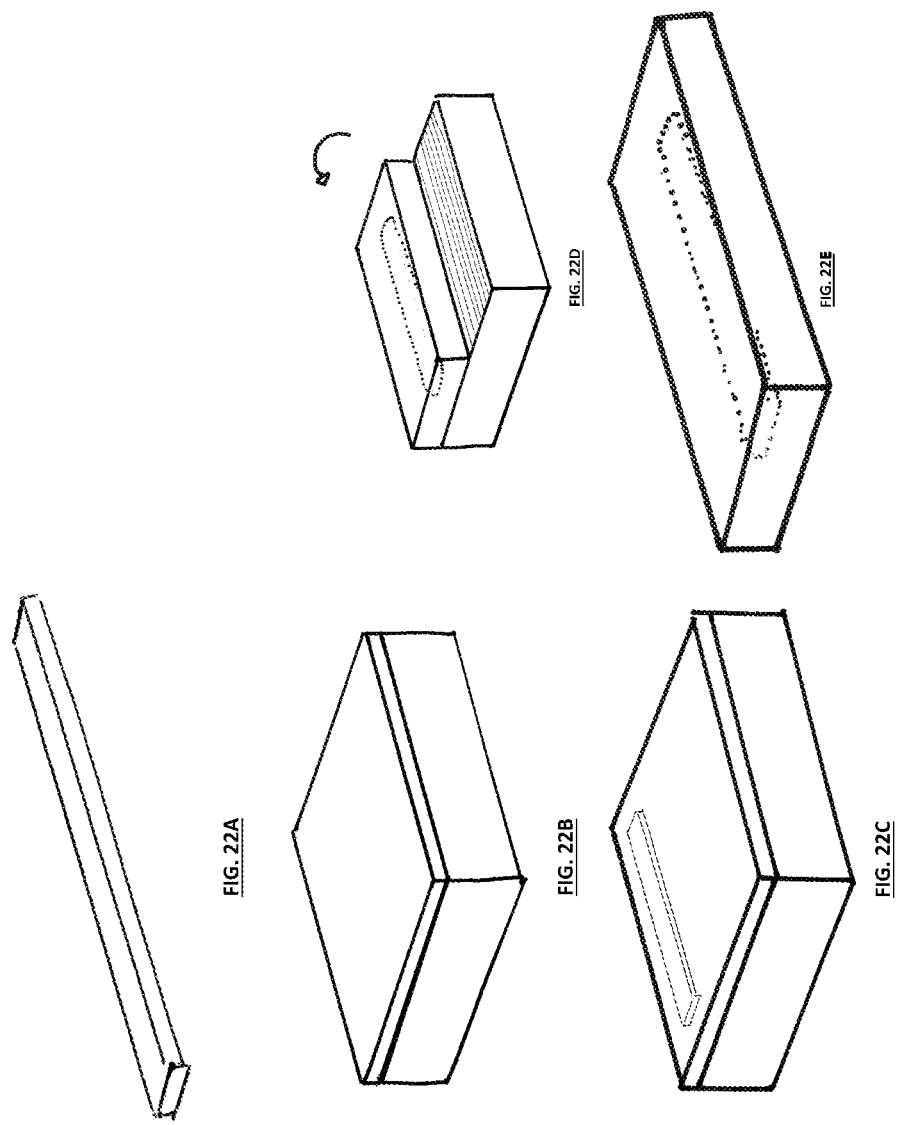

SYSTEM FOR GROWING FUNGAL MATERIALS

RELATED APPLICATIONS

This application is a Continuation application based on U.S. Nonprovisional application Ser. No. 17/326,742, filed May 21, 2021, and granted as U.S. Pat. No. 11,310,968 on Apr. 26, 2022, and which is a Continuation application based on U.S. Nonprovisional application Ser. No. 17/081,745, filed Oct. 27, 2020, and granted as U.S. Pat. No. 11,013,189 on May 25, 2021, and which is a Continuation application based on U.S. Nonprovisional application Ser. No. 15/884,788, filed Jan. 31, 2018 and granted as U.S. Pat. No. 10,842,089 on Nov. 24, 2020, which was a Continuation application of U.S. Nonprovisional application Ser. No. 15/650,779, filed Jul. 14, 2017 and granted Jun. 23, 2020 as U.S. Pat. No. 10,687,482, which claims priority to U.S. Provisional Patent Application 62/362,462, filed Jul. 14, 2017, the disclosures of which are incorporated herein by reference in their entirety.

BACKGROUND

The present disclosure relates generally to methods for growing fungal materials and objects therefrom, and in particular to a method for producing fungal materials and objects with variable shape, size, thickness, density, flexibility, and other predetermined qualities through directed and controlled tissue development and post-growth processing.

The material of a plant's body is formed from carbon and other elements filtered from the air, then bound together into sugars and other large molecules using energy from the sun. Mushrooms lack the ability to synthesize their bodies directly from sunlight and, like animals, need to consume things that were once alive in order to survive and grow. Filamentous fungi grow their bodies as an expanding and interconnected web of threadlike cells (called hyphae) directly within the food they are in the process of consuming as nutrients. The threadlike hyphae of the growing fungi exude strong enzymes and other agents into the wood or other substrate material it is living within and dissolves the molecular bonds that provide these substrates their structure. The fungus absorbs dissolved nutrients taken from the cellulose, lignin, and other substances present, which it then uses to build chitin, the resilient and strong protein that comprises its own hyphal walls. Chitin, like cellulose and keratin, is a naturally forming polymer that is found in the toughest organic tissues. In addition to being found in all fungi, chitin helps create the durable and flexible exoskeletons of insects and shellfish. These remarkable qualities are due in great part to the structure of the tissues' constituent parts as well as the properties of the materials that make them up.

Filamentous fungi have the natural tendency to join together smaller pieces of branching, colonial hyphae into a larger constituent whole, assembling and weaving strands and sheets of tissues called mycelium. Mycelium can adhere to, and possibly engulf, any other materials it comes in contact with through the extension of hyphae that use neighbor sensing and searching functions as guidance in their exploration into space beyond sources of nutritional sustenance. Like cement and plaster, fungal tissue will bind, harden and set into a variety of solidified configurations through the natural biological functions of mycelial growth and self-adhesion.

Fungal tissue can quickly be amplified to an enormous volume if provided with the appropriate living conditions. These conditions include the nutrients that might be available to the organism, the possible gas gradients within the growth environment and the humidity, light, and temperatures the organism might be exposed to as it takes form. Fungi are very sensitive to their surroundings, and by altering subtle factors it is possible to prompt their tissue to express a range of variably determined physical characteristics.

Fungi are very sensitive to chemicals present in their environment, and have the ability to alter the directions and vigor of growth of expanding hyphae as demonstrated through chemotaxic avoidance or attraction. Fungi are also very sensitive to other stimuli in their environment, and have the ability to alter directions and vigor of growth of expanding hyphae in response to gravitropic, thermotropic, thigmotropic, phototropic, and hydrotropic stimuli.

A substrate colonized with fungal hyphae, if provided adequate enclosure and environmental controls, will in a matter of one to three days generate a layer of fungal hyphae growing from the top of said substrate that will expand into space as a layer in a fuzzy and undifferentiated manner. This undifferentiated layer of hyphae, if left to continue growing, will soon advance in development and differentiate into specialized tissues determined to become fruit bodies or other sporocarp-producing structures.

Fungus-based materials and composites can be propagated on readily available agricultural waste, using principles and techniques that are well established with regard to growing filamentous fungi for human consumption and industry.

DESCRIPTION OF THE RELATED ART

Current forms of manufacturing of polymeric materials including animal skins and vinyl create environmental problems in manufacturing and recycling or disposal at the end of a material's utility. There is a need for new means of creating large volumes of polymeric materials that can be produced in ways that use fewer resources and otherwise diminish the environmental impacts of current practices.

Composite materials may be formed from fungus by mixing an inoculum including a preselected fungus with discrete particles and a nutrient material capable of being digested by the fungus. Furthermore, fungal primordium may be enclosed and grown in a mold to obtain a mass of fungal tissue in the form of low density chitinous material. Methods also exist for limiting the advancement of development of fungal tissues towards fruit bodies and sporocarp supporting structures through the administration of carbon dioxide/oxygen gradients and relative temperatures in which the organism is growing.

Unlike fungal tissue composites which are composed of lignocellulosic waste materials, fungal cellular tissue, and other ingredients, the fungal tissue materials and composites described herein can consist almost entirely of fungal tissues. This fungal material can be used in products that are currently made with ethylene vinyl acetate foams, polyvinyl chloride plastics, polyurethane foams, amongst others.

The state of the art in creating materials that are composed of fungal tissues in their manufacture is limited by the capacity of liquid or submerged cultures in the propagation of filamentous hyphae, which are then harvested and cultivated on secondary scaffolds and incubators. The method described herein can easily be adapted to the leading global method for producing fungal mycelium and edible mushrooms: solid state fermentation. Solid lignocellulosic substrates are easy to obtain, relatively inexpensive, and can be processed in extremely large volumes. Using solid-state nutrients allows for the making of 3-D molds and directly growing 3-D forms into pressed or otherwise structured and molded forms. This invention provides novel means of producing fungus based materials at larger volumes in size and scale, with greater determinations and controls for material function, using methodologies and hardware that are simpler and a more efficient means of production than are currently available.

In recent years, numerous methods and systems have been used for the large-scale production of composites grown with mycelium. Conventional methods for the production of materials made from fungal materials are limited:

Furthermore, conventional approaches do not produce a biologically active fungal tissue material. Most methods for producing pure samples of fungal tissue materials are reliant on submerged liquid cultures or rafts to cultivate significant volumes of hyphae, or require growing hyphae directly within a support matrix under very particular ecological control regimens. Without the use of a semi-permeable intermediate layer of material, the growing mycelium has been shown to unevenly generate, bind, and fuse to the heterogeneously ordered fibers that constitute the substrate, leading to a disrupted surface of the substrate, and high levels of heterogeneity and shear stresses in the growing sheet of fungal tissue. An intermediate layer can be considered as a layer through which fungal hyphae might grow or be prohibited to do so.

Additionally, conventional methods do not allow for easy manipulation of growing fungal hyphae to produce materials with desired qualities such as lattices, and other two or three-dimensional engineered structures as part of their constitution. Neither do conventional approaches account for post-growth processing of fungal tissue materials, without which the resulting outcome will exhibit poor mechanical characteristics when dry, particularly exhibiting low flexibility and high brittleness.

There is thus a need for a method for producing a fungal tissue materials formed of variable thickness, density and other qualities for use by various industrial processes and applications. Such a method would include an intermediate layer set upon a growing expression of hyphae from the surface of a colonized substrate. Such a method would include an intermediate layer that controls the interaction of the fungal material's structure with the substrate, for example by providing a membrane permeable to the fungal hyphae but not to substrate particles and fibers, thus allowing for easy separation of the two and eliminating additional processes for removing substrate particles and fibers from the harvested fungal materials. Such a method would include an intermediate layer that prevents the fungal material from permanently adhering to the substrate and which prevents damaging or tearing of the substrate when the fungal material is removed therefrom. Such a method would further allow the substrate to be reused for growing other fungal materials Such a method would further allow the manipulation of fungal materials to grow in particular and predetermined directions such as purposefully engineered structures, lattices, and other two or three-dimensional orientations of matter. Such a method would further allow the formation of multiple sheets of fungal material which can be stacked or arranged in a continuous form and finally, would be an inexpensive, simple, means of producing materials with less environmental impact than conventional methods.

SUMMARY OF THE INVENTION

Certain embodiments of the present invention provide methods for growing a fungus polymer matrix that is comprised predominately of fungal tissues. The resultant material is a flexible and soft, high-density amorphous polymer that can serve in applications that are currently served by synthetic plastics and foams as well as animal skins. The substrate utilized may comprise a mixture of discrete particles and nutrients and in some instances, is provided in an enclosure. A fungal inoculum may be prepared using a desired fungi strain. Hyphae from a defined species of filamentous fungi are propagated from a colonizable substrate that has been inoculated with said chosen fungi. Preferred species include the Ganodermas, the order Polyporales generally, and including all saprobic fungal candidates that derive sustenance from lignin and cellulose-rich sources. The fungal inoculum may be introduced into the substrate within the enclosure or prior to being introduced to the enclosure so as to provide an even distribution of the fungus throughout. The substrate is left to colonize. An intermediate layer is established on an open surface of the colonized substrate to control the interaction of the forming fungal tissue structure with the substrate. The presence of a uniform intermediate material atop the substrate enables a consistent surface from which the fungal tissues may grow, supporting uniform expansion of the fungal hyphae into the environment, and providing a determined space for manipulation by chemical and physical controls. Live fungal hyphae grow from the substrate and through the intermediate layer. In some instances, the living tissues that extend through the intermediate layer are manipulated to achieve a material having a desired thickness, shape, size and qualities.

The intermediate layer may be delaminated from the nutrient source out of which it has grown to terminate further growth of the material, or the fungal tissue layer may be delaminated from the intermediate layer, which is left in place and optionally reused. The resultant living fungal tissue structures may optionally be fused with other living fungal tissue structures to create two-dimensional and three-dimensional structures. The final fungal tissue may then be subjected to post-growth processing to achieve desired properties for downstream usage.

The fungal substrate precursor material may be cultivated in either batch or continuous processes and the fungal tissues may be modified and directed during growth in order to achieve uniform characteristics across a surface, or be engineered to take on distinct local qualities through manipulation of growing tissue, or the addition of particles, fibers, meshes, fabrics, and other additives, armatures, and components.

Fungal tissue sheets may be processed via cutting or other forming methods to obtain two-dimensional features and reliefs, or individual sheets may be stacked and grown together to form three-dimensional features, or composed with reinforcements or other structural amendments that may be incorporated into a growing tissue.

It is a first objective of the present invention to provide a method for producing a fungal materials and structures of variable shape, thickness, density, flexibility, and other predetermined qualities for industrial applications. Such a method includes the production of both two-dimensional and three-dimensional shapes by varying the shape of the enclosure, nutritive vehicle, intermediate layer and the conformation of produced fungal materials.

Another objective of the present invention is to provide an intermediate layer on an exposed surface of a substrate to promote uniform growth of fungal material.

Another objective of the invention is to provide an intermediate layer that may be separable from the substrate with minimal force and processes required.

Another objective of the invention is to provide an intermediate layer from which the fungal material may be easily separable and which remains attached to the substrate such that it may be re-used to grow additional fungal material.

Yet another objective of the invention is to provide an intermediate layer that prevents the fungal material from permanently adhering to the substrate and prevents damaging or tearing of the substrate when removing the fungal material.

Yet another objective of the invention is to provide a method that directs the growth of fungal material in particular and predetermined patterns such as orthogonal structures, lattices and other two or three-dimensional structures.

Yet another objective of the invention is to provide a method that allows for the fused growth of multiple fungal materials or structures, which can be stacked, folded, or otherwise arranged into 2D or 3D forms.

A yet another objective of the invention is to provide a method for adding composite materials to the fungal materials or structures to achieve desired material properties.

Yet another objective of the invention is to provide a method for processing the raw fungal material after growth to achieve desired characteristics such as improved flexibility and tensile strength.

Yet another object of the invention is to provide methods for creating an intermediate layer comprising a woven or porous surface that form a partial or complete laminate upon the surface of a colonized fungal substrate.

Yet another object of the invention is to provide a method for delaminating a fungal material with ease and lack of damage to the substrate that fueled the growth of said fungal material.

Yet another object of the invention is to provide a method for drying fungal materials (e.g. through using forced convection or conduction) to deactivate the fungus and prevent further growth.

Yet another object of the invention is to provide a method for the post processing of fungal materials to modify structure or chemical composition, thereby conferring physical qualities according to their desired application.

Yet another object of this invention is to provide a fungal biopolymer material for use in functional products.

Yet another object of the invention is to provide simple, economical techniques for making fungal biopolymer products.

Yet another object of the invention is to provide a method for the growing of a fungus-based polymer matrix.

Yet another object of the invention is to provide a method for the growing of a fungus-based polymer matrix in the form of a composite.

Yet another object of the invention is to provide a material that can act as an analog to synthetic plastic materials, foams, and animal skins.

These and other aspects, objects, and features of the present invention will be understood and appreciated by those skilled in the art upon studying the following specification, claims, and appended drawings.

The following detailed description together with accompanying figures will provide a better understanding of the nature and advantages of the present invention.

DESCRIPTIONS OF THE FIGURES

In order to enhance clarity and improve understanding of the various elements and embodiments of the invention, elements in the figures have not necessarily been drawn to scale. Furthermore, elements that are known to be common and well understood to those in the industry are not depicted in order to provide a clear view of the various embodiments of the invention. Thus, the drawings are generalized in form in the interest of clarity and concision.

FIG. 5C illustrates a composite material being placed onto fungal material that has grown through the intermediate layer in accordance with the preferred embodiment of the present invention;

FIG. 6A illustrates the composite material on top of the fungal material and intermediate layer and an enclosure lid with a plurality of openings in accordance with the preferred embodiment of the present invention;

FIG. 6B illustrates fungal tissue grown through the composite material and the enclosure lid with a plurality of openings in accordance with the preferred embodiment of the present invention;

FIG. 15A is a first cross-sectional view of fungal material and void spaces;

FIG. 15B is a second cross-sectional view of fungal material and void spaces;

FIG. 15C is a third cross-sectional view of fungal material and void spaces;

FIG. 15D is a fourth cross-sectional view of fungal material and void spaces;

FIG. 15E is a fifth cross-sectional view of fungal material and void spaces;

FIG. 15F is a sixth cross-sectional view of fungal material and void spaces;

FIG. 15G is a perspective view of fungal material and void spaces;

FIG. 16A illustrates part one of an eleven-part alternative method involving agitation of the fungal material;

FIG. 16B illustrates part two of an eleven-part alternative method involving agitation of the fungal material;

FIG. 16C illustrates part three of an eleven-part alternative method involving agitation of the fungal material;

FIG. 16D illustrates part four of an eleven-part alternative method involving agitation of the fungal material;

FIG. 16E illustrates part five of an eleven-part alternative method involving agitation of the fungal material;

FIG. 16F illustrates part six of an eleven-part alternative method involving agitation of the fungal material;

FIG. 16G illustrates part seven of an eleven-part alternative method involving agitation of the fungal material;

FIG. 16H illustrates part eight of an eleven-part alternative method involving agitation of the fungal material;

FIG. 16I illustrates part nine of an eleven-part alternative method involving agitation of the fungal material;

FIG. 16J illustrates part ten of an eleven-part alternative method involving agitation of the fungal material;

FIG. 16K illustrates part eleven of an eleven-part alternative method involving agitation of the fungal material;

FIG. 17A illustrates a first of various steps involving the alteration of the fungal material via displacement of fungal material and regrowth of surrounding fungal material;

FIG. 17B illustrates a second of various steps involving the alteration of the fungal material via displacement of fungal material and regrowth of surrounding fungal material;

FIG. 17C illustrates a third of various steps involving the alteration of the fungal material via displacement of fungal material and regrowth of surrounding fungal material;

FIG. 17D illustrates a fourth of various steps involving the alteration of the fungal material via displacement of fungal material and regrowth of surrounding fungal material;

FIG. 17E illustrates a fifth of various steps involving the alteration of the fungal material via displacement of fungal material and regrowth of surrounding fungal material;

FIG. 17F illustrates a sixth of various steps involving the alteration of the fungal material via displacement of fungal material and regrowth of surrounding fungal material;

FIG. 17G illustrates a seventh of various steps involving the alteration of the fungal material via displacement of fungal material and regrowth of surrounding fungal material;

FIG. 17H illustrates an eighth of various steps involving the alteration of the fungal material via displacement of fungal material and regrowth of surrounding fungal material;

FIG. 17I illustrates a ninth of various steps involving the alteration of the fungal material via displacement of fungal material and regrowth of surrounding fungal material;

FIG. 17J illustrates a tenth of various steps involving the alteration of the fungal material via displacement of fungal material and regrowth of surrounding fungal material;

FIG. 18A is a perspective view of a first step of an optional method wherein the surface plane of the growing fungal material is embedded with discrete fibrous elements;

FIG. 18B is a perspective view of a second step of an optional method wherein the surface plane of the growing fungal material is embedded with discrete fibrous elements;

FIG. 18C is a perspective view of a third step of an optional method wherein the surface plane of the growing fungal material is embedded with discrete fibrous elements;

FIG. 18D is a perspective view of a fourth step of an optional method wherein the surface plane of the growing fungal material is embedded with discrete fibrous elements;

FIG. 19A is a perspective view of a first step of an optional method wherein the surface plane of the growing fungal material is embedded with discrete particles;

FIG. 19B is a perspective view of a second step of an optional method wherein the surface plane of the growing fungal material is embedded with discrete particles;

FIG. 19C is a perspective view of a third step of an optional method wherein the surface plane of the growing fungal material is embedded with discrete particles;

FIG. 19D is a perspective view of a fourth step of an optional method wherein the surface plane of the growing fungal material is embedded with discrete particles;

FIG. 20A illustrates a first step in the process of forming and fusing a three-dimensional fungal object in the form of a tube shaped around a solid cylinder, in this instance while remaining attached to a nutritive vehicle;

FIG. 20B illustrates a second step in the process of forming and fusing a three-dimensional fungal object in the form of a tube shaped around a solid cylinder, in this instance while remaining attached to a nutritive vehicle;

FIG. 20C illustrates a third step in the process of forming and fusing a three-dimensional fungal object in the form of a tube shaped around a solid cylinder, in this instance while remaining attached to a nutritive vehicle;

FIG. 20D illustrates a sectional view of the same object taking form as illustrated in FIG. 20A-20C, with nutritive vehicle, intermediate layer, cylindrical form, and overlapping and joined elements of the fungal material resting upon the cylinder;

FIG. 21A illustrates a first step of a method for growing fungal material in a targeted three-dimensional form (in this case a hemispherical shape), with a view of the object growing in a controlled and administrable environment;

FIG. 21B illustrates a second step of a method for growing fungal material in a targeted three-dimensional form (in this case a hemispherical shape);

FIG. 21C illustrates a cross sectional view of the first step of a method for growing fungal material in a targeted three-dimensional form (in this case a hemispherical shape);

FIG. 21D illustrates a cross sectional view of a second step of the method for growing fungal material in a targeted three-dimensional form (in this case a hemispherical shape) illustrated in FIG. 21A-21B;

Figure 1:
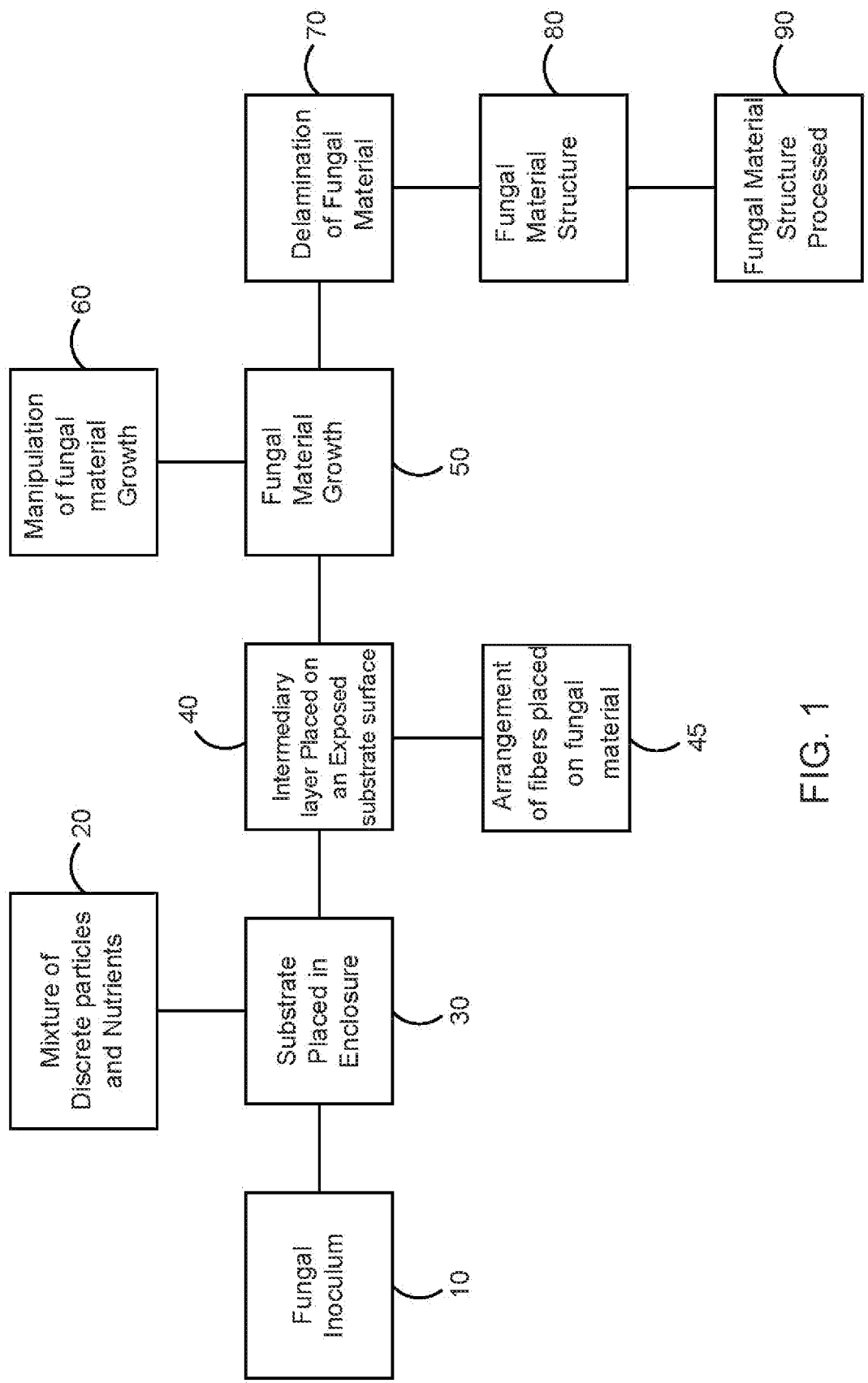
FIG. 1 illustrates a block diagram of a method of producing fungal material in accordance with the preferred embodiment of the present invention.

FIG. 21D illustrates a cross-sectional view of a second step of the method for growing fungal material in a targeted three-dimensional form (in this case a hemispherical shape) illustrated in FIG. 21A-21B; and FIG. 22A illustrates a first of multiple steps in the formation of a fungal object wherein a composite material is placed on a fungal material and a portion of said fungal material is delaminated from the intermediate layer, folded to encase the composite material, and fused with the portion of the fungal material left in contact with the intermediate layer and underlying nutritive vehicle;

FIG. 22B illustrates a second of the multiple steps detailed with respect to FIG. 22A;

FIG. 22C illustrates a third of the multiple steps detailed with respect to FIG. 22A;

FIG. 22D illustrates a fourth of the multiple steps detailed with respect to FIG. 22A; and FIG. 22E illustrates a fifth of the multiple steps detailed with respect to FIG. 22A.

DETAILED DESCRIPTION OF THE INVENTION

The forthcoming descriptions of the present invention have been presented for the purpose of illustration and description. It is not intended to be exhaustive or to limit the invention to the precise form disclosed. Many modifications and variations are possible in light of the above teachings. It is to be understood that other embodiments may be utilized and changes may be made without departing from the scope of the present invention, and that the scope of the present invention not be limited by this detailed description, but by the claims and the equivalents to the claims appended hereto.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term "about" means +/−5% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

For the specification, the following terms shall apply.

Administrable space: A volume in which the orientation of fungal hyphae can be directed, e.g. through physical manipulation, chemical manipulation, or phototropic, skototropic, or optogenetic control.

Composite material: Any material not the same as a fungal tissue that comes into contact with said fungal tissue. Composite material may thus consist of fungal tissue.

Growth pattern of hyphae: The micro- and macro-structures of the materials that make up the hyphae, e.g. the arrangement of chitin molecules, the thickness of hyphal walls, the number of branches, the amount of hyphal fusion, and the orientation of the hyphae Hyphae: The branching filaments that make up a fungal tissue.

Hyphal fusion: The biological process by which fungal hyphae join, also known as hyphal anastomosis. A form of fused growth.

Nutritive vehicle: A substance capable of providing nutritional resources for the growth and metabolic processes of a fungal tissue.

Porous material: A material with any number, shape, and orientation of zones permeable to fungal growth but not to the nutritive vehicle.

Turning first to FIG. 1, a block diagram of a method of producing a fungal structure for industrial applications in accordance with the preferred embodiment of the present invention is illustrated. One method of making the fungal material structure 80 includes providing a nutritive vehicle 30 having a mixture of discrete particles and nutrients 20 in an enclosure. A fungal inoculum 10 is prepared, which is made up of a desired fungi strain, which can be any vegetative, sexual, or asexual structure of a fungus that is capable of growing a new fungal colony. The fungal inoculum 10 needs the nutrients 20 to grow, and which are blended with the nutritive vehicle 30. Thus, the fungal inoculum 10 is introduced into the nutritive vehicle 30 within the enclosure, which provides an even distribution of the fungus throughout. An intermediate layer 40 is placed on a surface of the nutritive vehicle 30, providing a medium through which fungal hyphae might grow or be prohibited thereof 50 and preventing the expressed fungal material 50 from permanently adhering to the nutritive vehicle 30. Live fungal material 50 is grown from the fungal inoculum 10 on the nutritive vehicle and through the intermediate layer, and grows in a direction away from the exposed face of said nutritive vehicle. 30. An arrangement of fibers is optionally placed on the surface of the newly grown fungal material atop the intermediate layer as shown at block 45. Live fungal material is directed to grow through these fibers and form a composite material with enhanced material properties. Throughout growth, live fungal material 50 is manipulated as indicated at block 60 to achieve a desired thickness, shape, size and quality of fungal material. The intermediate layer 40 is delaminated as indicated at block 70 to terminate further growth of the fungal inoculum 10, thereby obtaining the fungal material 80, which can be processed for further use as indicated at block 90.

Figure 2:
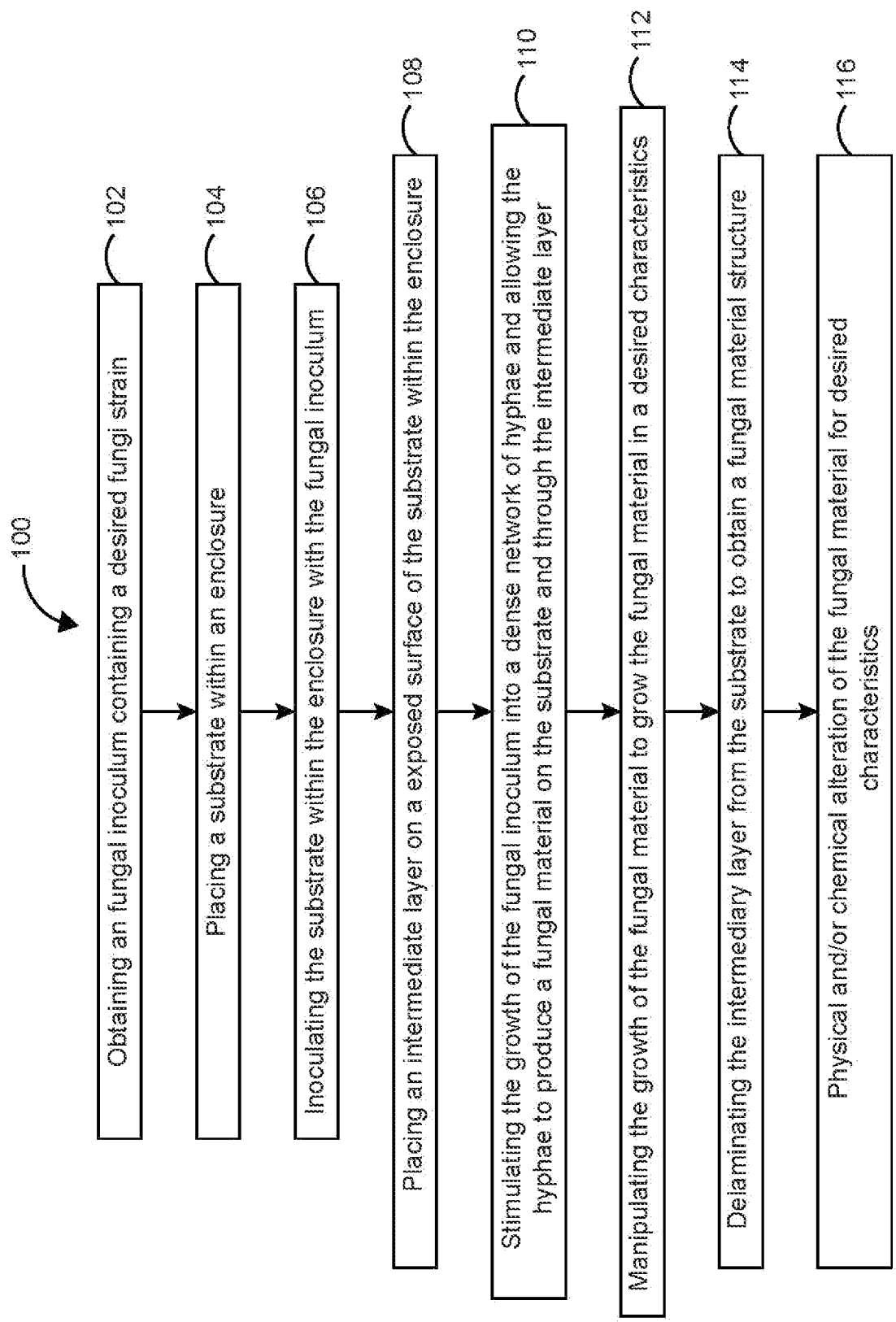
FIG. 2 illustrates a flowchart of the method of producing fungal material in accordance with the preferred embodiment of the present invention.

In FIG. 2, a flowchart 100 illustrates the method of producing the fungal material for industrial applications in accordance with the preferred embodiment of the present invention. The method comprises the steps of: obtaining a fungal inoculum comprising a desired fungi strain as indicated at block 102, placing a nutritive vehicle within an enclosure as indicated at block 104, inoculating the nutritive vehicle within the enclosure with the fungal inoculum as indicated at block 106, placing an intermediate layer on the top surface of the nutritive vehicle within the enclosure as indicated at block 108, placing an optional additional material on top of the intermediate layer and/or mycelial layer, throughout which fungal material can grow to form a composite material, stimulating the growth of the fungal inoculum into a dense network of hyphae and allowing the hyphae to produce the fungal material on the nutritive vehicle and the intermediate layer as indicated at block 110, periodically manipulating the growth of the fungal material to grow the fungal material with desired characteristics as indicated at block 112, delaminating the intermediate layer from the nutritive vehicle to obtain a fungal material structure as indicated at block 114, and processing the fungal materials for various industrial applications as indicated at block 116.

Nutritive Vehicle

The nutritive vehicle 30 includes discrete particles and nutrients that allow the desired fungi strain to grow over a period of time by digesting the nutrients. The nutritive vehicle 30 is any material adequate to provide for the growth of the fungal material 50. A nutritive vehicle 202 can be a ligno-cellulosic material with appropriate pH balance and other nutrients commensurate for the propagation of a desired fungi strain.

Fungal Inoculum

A fungal inoculum is an amplifiable colony of a desired fungal strain. The fungal species is preferably selected from the fungal kingdom order Polyporales, the Family Ganodermataceae, with preference to the *Ganoderma lucidum, Ganoderma tsugae, Ganoderma applanatum, Ganoderma resinaceum, Ganoderma oregonense*. Other preferred candidate include *Trametes versicolor, Trametes pubescens, Schizophyllum commune*, and Polyporous squamosus. The desired fungi strain is propagated throughout the nutritive vehicle so that it is fully colonized by the fungal mycelium. In one method, the fungi may be propagated by application to pasteurized nutritive vehicle within sealed plastic bags with micropore membranes (for atmospheric regulation).

Growth Enclosure

A growth enclosure can be any type of container adapted for culturing cells, bacteria, and/or mycelia and that can contain the nutritive vehicle while minimizing opportunities for infection and allowing for the control of environmental factors such as temperature, humidity, light levels, and $CO_2$ and $O_2$ concentrations.

Fundamental is that the enclosure controls air exchange and $O_2$, directing the growth to only specific areas through access to atmosphere, e.g. through the intermediate layer.

The enclosure is used to contain the nutritive vehicle. In one embodiment, the nutritive vehicle 30 is uniformly distributed in an enclosure and leveled to substantially form a plane normal to the direction of the fungal materials growth 50, aiding in the even and uniform growth of resultant planar fungal material.

The inoculum of the desired fungi strain 10 can be partially or fully colonized throughout the nutritive vehicle 30 within the enclosure.

The enclosure and the exposed surface of the nutritive vehicle 30 may be formed into one of or any combination of planar and non-planar surfaces to determine the shape of the resultant fungal material.

Intermediate Layer

The intermediate layer 40 is placed on an exposed surface of the nutritive vehicle 30 and is intended to physically isolate the growing fungal material from the nutritive vehicle. It can take the form of a membrane or fabric that is permeable to the growing fungal material 50 but not to the particles of the nutritive vehicle. It enables uniform growth of the fungal material 50 by providing uniform initial conditions of growth and enables the fungal material 50 to be cleanly removed without damaging the nutritive vehicle 30 during the delamination process 70.

The intermediate layer 40 facilitates uniform separation of the fungal material 50 from the nutritive vehicle 30 by controlling the interaction of the nutritive vehicle with the fungal material. Thus, the intermediate layer 40 prevents the fungal material 50 from permanently adhering to the nutritive vehicle 30, and damaging or tearing of the nutritive vehicle 30 when removing the fungal material 50. The nutritive vehicle 30 can thus be reused to grow additional mycelial structures. Said again, when the living fungal tissue has been removed from the nutritive vehicle from which it has grown, it can be reattached to the same or similar nutritive vehicle, then allowed to reform as a result of natural bonding and fusing of fungal hyphae. This can be a somatic clonal type, or might be differentiated sexually, or by different species. The intermediate layer 40 may be fully or partially permeable across its surface. Growth of fungal material will be blocked in impermeable areas, allowing for masked or patterned growth.

In one embodiment, the intermediate layer is a stand-alone component separate from the enclosure and the nutritive vehicle. In another embodiment, the intermediate layer is attached to or is permanently a part of the enclosure. In another embodiment, the intermediate layer 40 is embedded within the nutritive vehicle 30.

The material of the intermediate layer 40 may comprise lignin or other biodegradable compounds to interact with the mycelium 50. In an alternate embodiment, the material of the intermediate layer 40 comprises a polymer that is not degraded by the fungi.

In certain embodiments, the intermediate layer is formed in situ. In these embodiments, an intermediate layer can be created on top of the colonized nutritive vehicle through heat or chemical polymerization of the cellulose, chitin and other components of the nutritive vehicle. In an alternative embodiment, a thin initial layer of mycelial growth on the exposed surface of the nutritive vehicle can be modified by physical tending of the growing tissue or by applications of heat, chemical treatments, and/or powders, gels, or other materials to create an intermediate layer.

The intermediate layer may be designed to accept controls by various means (including electrical actuation) to allow for the application of dynamic filtering functions to growing fungal tissue Controlling Growth The fungal material 50 may be periodically manipulated 60 to direct growth in ways that confer desired characteristics, including density, evenness, and higher strength. Without careful tending, the fungal material 50 will differentiate into sclerotic tissues, primordium, fruiting bodies, and other tissues. It is critical to maintain control through careful manipulation to obtain uniformly grown mycelial structures with desired characteristics. The periodic alteration of morphology in the apical extension of a colony of growing fungal hyphae acts as an inhibiting agent on localized developmental pathways of that tissue.

The growth of the mycelium 50 is directed by direct means and passive means. The direct means of manipulations 60 comprise intentional changes through the application of pressure, ablation, abrasion, cutting, chemical additives, and/or electromagnetic stimulation and other methods. The passive means of manipulations 60 may be achieved through control of environmental conditions and/or the composition of the nutritive vehicle. In the preferred embodiment, both means of manipulation 60 are used.

Various growth compounds and fungal hormones exist, such as 10-oxo-trans-8-decenoic acid (ODA), that can be used to change growth characteristics as is desired. Chemical supplements, such as forskolin, may also be added to the nutritive vehicle, or misted onto the surface of growing fungus materials. Finally, growing the material through an intermediate layer with a controlled electric field can allow one to induce, prohibit, or otherwise act to determine characteristics of growing tissues. All of the techniques can be used to address and alter the growing material and its final characteristics.

The orientation of fungal hyphae changes the morphology of the tissue and thus the mechanical characteristics of the material. As the tissue grows in periodic layers, it is possible to orient the growth of layers in succession to thus create structures at microscopic and macroscopic levels of the fungus material composite, and to produce different material characteristics as a result.

The composition and growth habits of growing hyphae can be directed by various means. For example, protein inhibition and/or osmotic shock can increase the normal synthesis of chitin, which could have significant implications for material strength.

The environment can be controlled in many ways to affect local and globalized growth of the fungal material 50, including through the structure of the enclosure and any lid applied to the exposed surface. In one instance, the control of light frequency and intensity is essential as a means of control.

In the instance that intentional inconsistencies are desired within the product, disturbances across the plane of growth can be induced through environmental controls and application of various physical and chemical treatments. In one embodiment, differing environmental controls are applied to particular regions of the growing material to create specific desired and localized effects. For example, the relative concentrations of gaseous O2 and CO2 can be used to create desired growth habits. In another instance, control of temperature can be used to similar effect. In another instance, aspirated air applied to areas of the growing surface can be used to prevent or promote certain developments of the growing fungal organism.

Aspects of the colonized nutritive vehicle might be intentionally organized to control the growth of the fungal tissues, including the distribution of nutrients within the nutritive vehicle, the intentional use of antibiotics and other agents for masking, and the application of other amendments to inhibit and/or promote various types of growth. Other environmental responses of the organism (gravitropism, phototropism, etc.) may be used to control growth, both through active control of the growth environment, or by passive control from the design and organization of the growth environment.

The manipulation 60 of the fungal material 50 can be performed by physical means. In one instance, the hyphae are flattened and laid in one direction using a roller. The roller depresses the hyphae into a planar form. When the hyphae regrow, they express an arbuscular form, and the rolling method is used to weave the body of the fungal material 50 into novel patterns. Due to such physical manipulation 60 of the fungal material 50, the hyphae can be grown into particular and determined directions such that they can be arranged into orthogonal structures, lattices, and other two-dimensional and three-dimensional organizations. With the consistent and patterned manipulations 60 of hyphal growth with this method, the fungal material 50 can be formed in layered structures with determined arrangements of fungal tissue (e.g. alternating layers with orthogonally-arranged fibers). In addition to determining the structure of the hyphal network, this form of manipulation also homogenizes the mycelial tissue by deterring it from differentiating and developing primordia or other tissues.

In another embodiment of physical manipulation, the mycelial tissues may be periodically scratched and/or furrowed to create a fungal material structure with highly intergrown layers. The resulting entanglement between adjacent layers and the high surface area of the interlayer surface contributes to resistance to delamination between individual layers.

In another embodiment, the growth of the hyphae is stimulated by light at the macroscopic level. In yet another embodiment, the growth of the hyphae at the cellular level is controlled by the use of optical signals and fungal strains that are genetically-modified to respond to such signals.

In an alternate embodiment, water, liquid solutions, gels and other viscous agents may be deposited on the growing surface of the fungal tissue in determined volumes and distributions. These agents affect localized conditions by encouraging or inhibiting the growth and extension of fungal hyphae. Through this deposition of viscous agents, localized and emergent tissue development can be affected with determination and fidelity. Hydrostatic charges on said deposited viscous agents also have influence over the behavior and direction of apically extending hyphae above the tissue surface.

Growth of Composite Materials

In an alternative embodiment, to direct growth and/or produce composite materials, materials may be incorporated into the growing fungal tissue while the fungal material is still viable. In one embodiment, cellulose-based, synthetic or other organic fibers including various textile forms (e.g. woven, knit, fulled, felted) of preferred lengths and structural characteristics are deposited on the exposed surface of the growing fungal tissue, allowing for the growth of a composite material. The composition and organization of the composite fibers enables the fungal tissue to be engineered, enhancing mechanical properties of the overall material including tensile and compressive strength.

In an alternate embodiment, fungal tissue can be grown through 2D and 3D matrices and objects of various materials to create composites with desired characteristics and qualities. This added layer of material may be composed of any material that fungal cells can grow through (pore size larger than 1 micron). These layers may be pressed onto or near the surface of the growing cells or otherwise impressed upon its surface, or placed between two or more layers of growing fungal material, such that these reinforcement layers are then incorporated into the fungal tissue.

A further laminate may be bound to the fungal tissue that has grown into reinforcing elements and layers by attaching said laminate to the growing composite, which enables a method of binding all the layers together as a result.

Delamination

During the delamination process 70, it is possible to pull the fungal material 50 off the intermediate layer 40 in a manner that the intermediate layer 40 remains adhered to the nutritive vehicle 30 and provides subsequent secondary and further growth of the fungal material 50. Thus, multiple sheets of fungal material 50 can be produced during the process.

An alternative embodiment of the invention involves the reapplication of the delaminated fungal material 70 onto the same nutritive vehicle 30, but in a different geometric orientation. Yet another instance involves the reapplication of the delaminated fungal material 70 onto a nutritive vehicle inoculated with a different type of fungus. The produced fungal material 80 can then be processed for use by various methods described below.

Fused Growth

Hyphal fusion is one mechanism by which fused growth can occur. It is the biological process by which distinct and compatible fungal hyphae join, also known as hyphal anastomosis. This process can be stimulated and directed for the production of novel materials.

Living mycelial sheets may be used as-is, or the sheet and any number of sheets can be joined with portions of itself or other living fungal material structures by stimulating growth with the applications of pressure and availability of nutrients.

In a preferred embodiment, multiple living sheets are stacked together and set with a weight or pressure such that at least one sheet or portion thereof is in contact with a mass of nutrient nutritive vehicle and is incubated until these components fuse into a cohesive structure.

In an alternate embodiment, living mycelial structures may be shaped or formed into 3D objects and incubated until these components compose a uniform object or fuse together in a desired way.

In one instance, any living fungal material 50 can be delaminated from its nutritive vehicle and combined together with another structure or many other structures, such that in some cases the fungal tissue self-adheres, which causes fusing at a cellular level. In one instance, many structures may be combined to create complex self-adhered shapes or sheets. Alternatively, areas of a single sheet of fungal material 50 can be joined together to generate a 2D or 3D form.

For fusing to occur, the living tissues must have access to nutrients to fuel growth. In one embodiment, this can be achieved by leaving the material partially attached to the nutritive vehicle from which it has been generated, arranging it so that the areas desired to fuse together are made to come into contact with one another, applying pressure sufficient to produce close contact between the areas, and allowing the material enough time to grow a complete bond.

In one instance of the invention, a sheet of fungal tissue is grown by means of fungal hyphae expressed through an intermediate and perforated layer into the form of a layer within a growing environment. This environment and hyphae are administrated to create a fungal material or composite of a desired thickness and order, upon which a part or half of said sheet of material is delaminated from the intermediate layer, and folded in such a manner that the delaminated aspect of the layer is put into as close contact as is possible with the fungus tissue still connected to the intermediate layer. If such an altered version of the growing artifact is left for a period as short as 24 hours, the hyphae from the top part of the fungal tissue material will fuse to the hyphae of the layer beneath it, growing into a joined mass.

Additionally, scoring, pricking, manipulating the surface or otherwise altering the surface qualities of the areas to be fused may alter the mechanical properties of the produced material, such as by increasing the bonded strength of multiple laminated sheets of material, creating void spaces, lattices, and other internal artifacts structured through such intentional growth.

In another embodiment, non-fungus materials can be fused between fungus based materials to serve the purpose of structural reinforcements or other modifications to the performance and aesthetics of the fungus based materials.

Post-Growth Processing

The sheet of fungal material may be treated in such a manner as to make it pliant and resilient towards the uses of industry. Without such processing, the resultant material can be highly brittle, weak, and generally of low utility. The processing can be performed by drying, providing mechanical stress, and adding plasticizers, water-proofing agents, cross-linking agents and other additives. The fungal material made in accordance with the invention may be subjected to further processing steps to achieve a desired final product for various industrial processes and applications.

If left untreated, the material can become brittle when dry. Should a flexible dry state be desired, the material can be treated with a biodegradable plasticizing agent and/or worked mechanically throughout the drying process. In one embodiment, the plasticizing agent can be one of any number of polyols typically used as plasticizers for chitin- and chitosan-bearing materials, such as propylene glycol. Such plasticizers can be applied to the material by rubbing, spraying, or soaking with or without dilution by water or other solvents. The material may also be rendered flexible by working it mechanically throughout the drying process with or without the application of oils, plasticizing agents, or other additives.

The material may also be chemically cross-linked at the molecular level to improve material qualities such as tensile strength and flexing endurance. In one embodiment, this is achieved through the application of tanning compounds (such as pyrogallols and catechols) and aldehyde compounds (such as glutaraldehyde). In another embodiment, this is achieved through the cross-linking between amine groups in the fungal chitin and/or chitosan molecules.

The material can be pressed with or without heat to obtain desired thicknesses and surface qualities. In one embodiment, the material is dried and pressed between heated plates at temperatures greater than 200 F to compress the material, achieve an even surface, and impart a desired surface texture.

The material can be treated with waterproofing or water-resistance agents before, during, or after pressing, or at any stage in the production of the material to impart greater water-resistance to the material and greater water-fastness to the properties of the material. In one embodiment, the material is coated in a paste made from a mixture of natural oils and waxes and heated with or without pressure to achieve penetration.

At various points in this process, the material may be dyed or otherwise finished aesthetically as desired. Dyes, for example, can be applied before, after, or during the plasticizing step through painting, spraying, or soaking with or without the presence of water or other solvents. In another embodiment, the surface textures can be altered by abrasion, rolling, or other means.

The following examples reflect certain embodiments of the invention. The method components in the examples may be presented as steps; however, unless specifically stated, any one step need not occur before or after any other step. Furthermore, in certain embodiments of the invention, certain steps may be omitted or repeated.

Example 1—The following example describes one method for producing a flat sheet of fungal material with an embedding composite material for reinforcement.

Step 1—Obtaining inoculated nutritive vehicle—The nutritive vehicle may consist of at least one of straw, hay, hemp, wool, cotton, rice hulls, recycled hardwood/softwood sawdust, water, calcium carbonate, nitrogen, sugar rich grains, and shrimp shells.

A given nutritive vehicle of a combination including the above materials is pasteurized and let to cool to room temperature. A tissue culture of the desired fungi strain is introduced and left to propagate throughout the nutritive vehicle. The pasteurization process eliminates or limits competition as the fungus is colonizing the nutritive vehicle. This step is referred to as the colonization of the nutritive vehicle.

Figure 3:
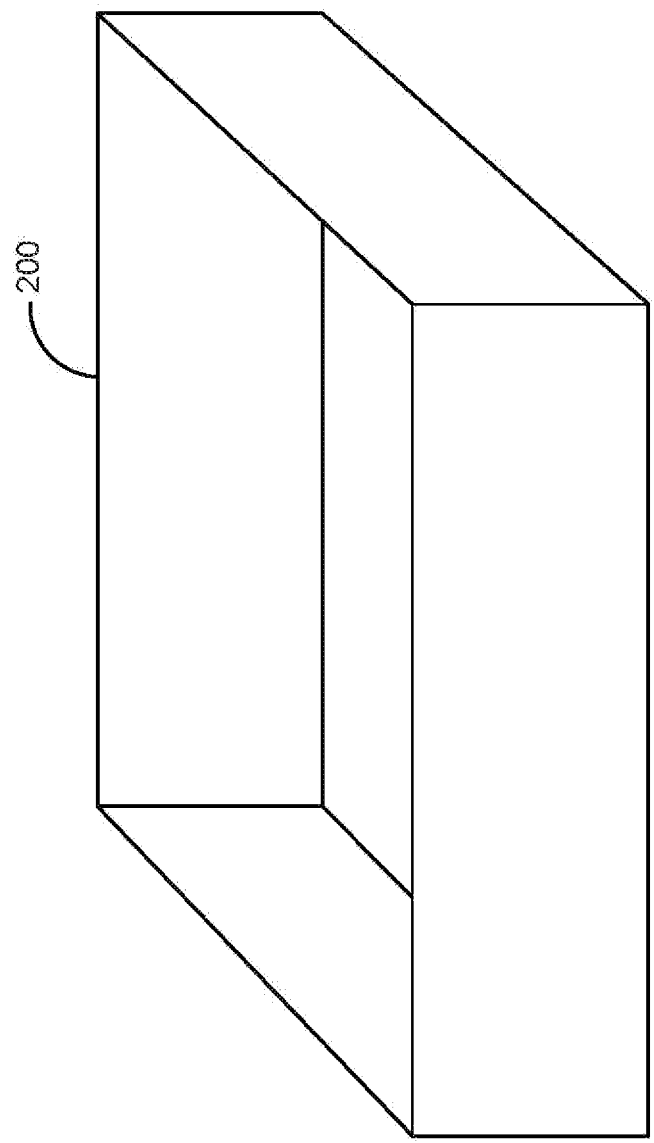
FIG. 3 illustrates an enclosure for placing a nutritive vehicle in accordance with the preferred embodiment of the present invention.

Step 2—Loading nutritive vehicle into growth enclosure—Showing a preferred embodiment, FIG. 3 illustrates a box-like enclosure 200 for placing a nutritive vehicle in accordance with the preferred embodiment of the present invention. The box-like enclosure 200 may in one embodiment comprise a plywood box measuring 3'×3'×8", which is lined with 3 mil plastic sheeting. In one embodiment of the present invention, the enclosure 200 consists of a single compartment. In another embodiment of the present invention, the enclosure 200 comprises a plurality of compartments.

Figure 4:
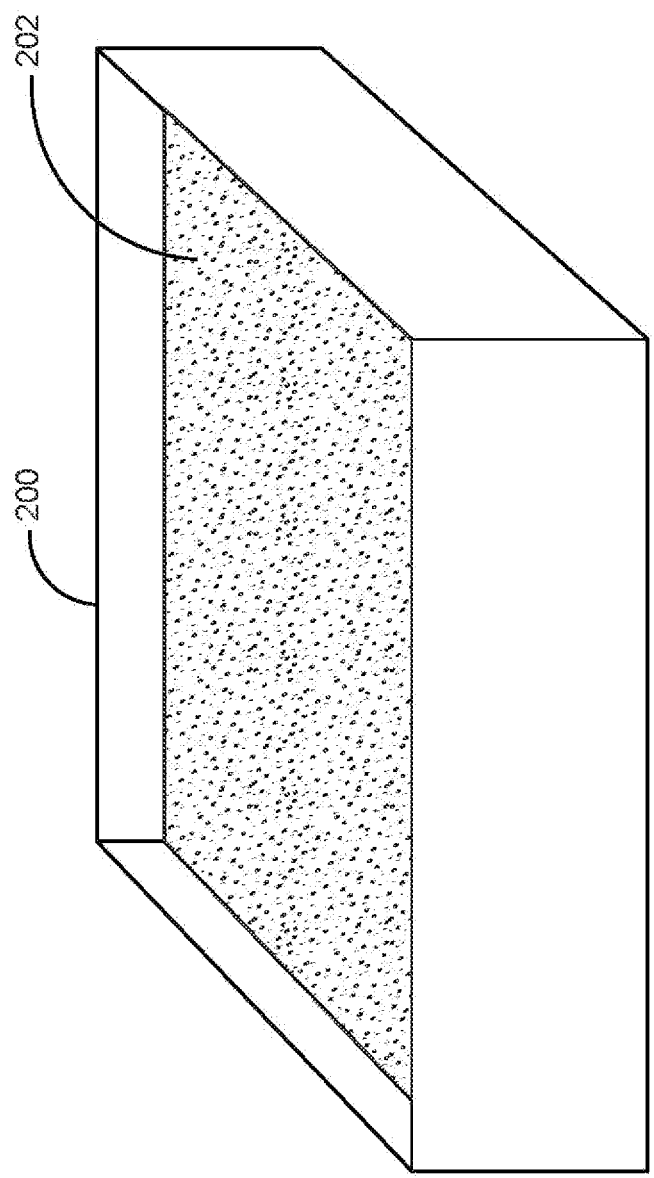
FIG. 4 illustrates the nutritive vehicle placed within the enclosure in accordance with the preferred embodiment of the present invention.

FIG. 4 illustrates the nutritive vehicle 202 placed within the enclosure 200 in accordance with an embodiment of the present invention.

In one embodiment, 60 liters of colonized nutritive vehicle is placed into the enclosure. The nutritive vehicle is evenly distributed at a depth of 4-6", and flattened with pressure such that the top surface of the nutritive vehicle forms a flat and even surface.

Figure 5A:
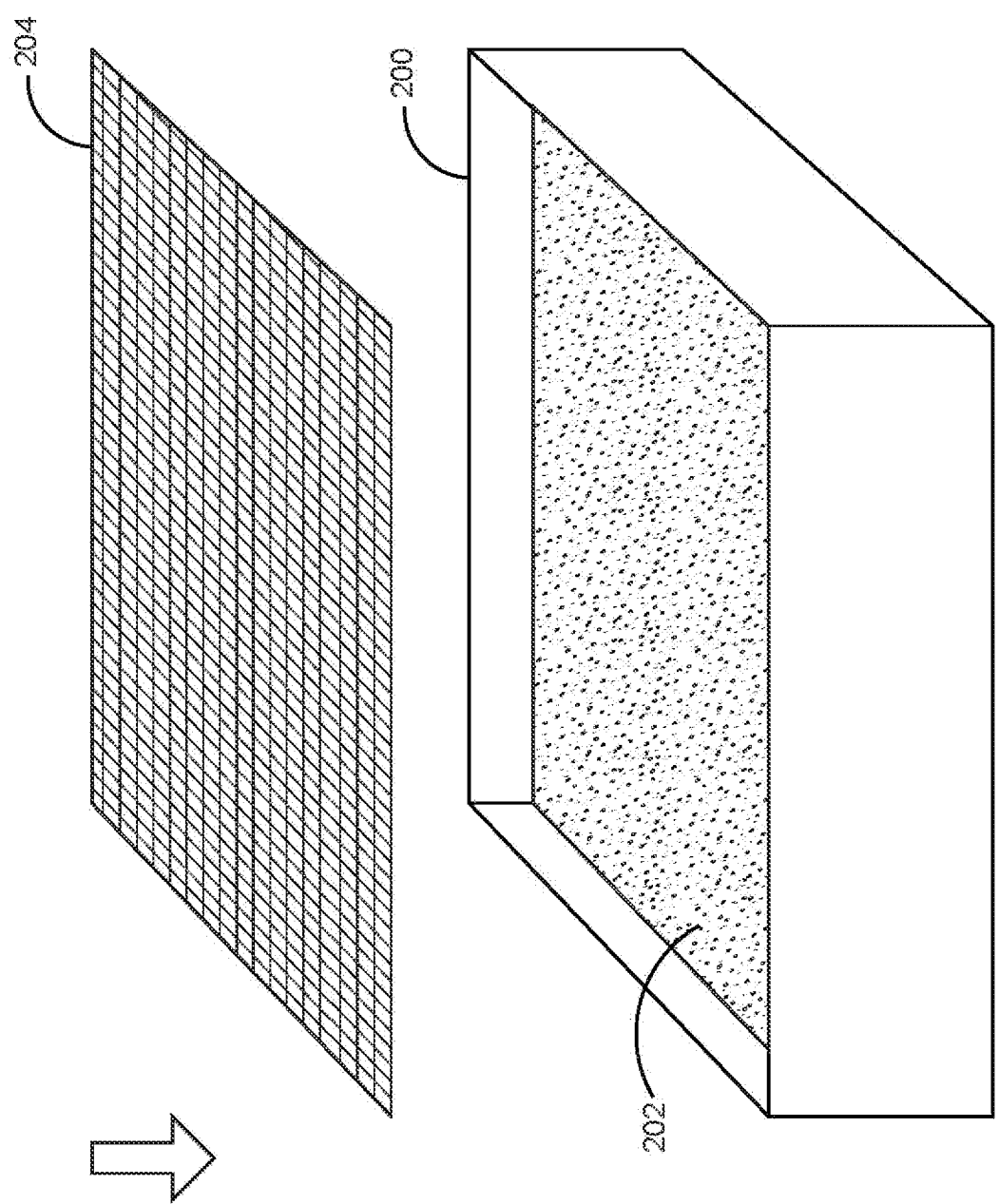
FIG. 5A illustrates an intermediate layer being placed on an exposed surface of the nutritive vehicle in accordance with the preferred embodiment of the present invention.
Figure 5B:
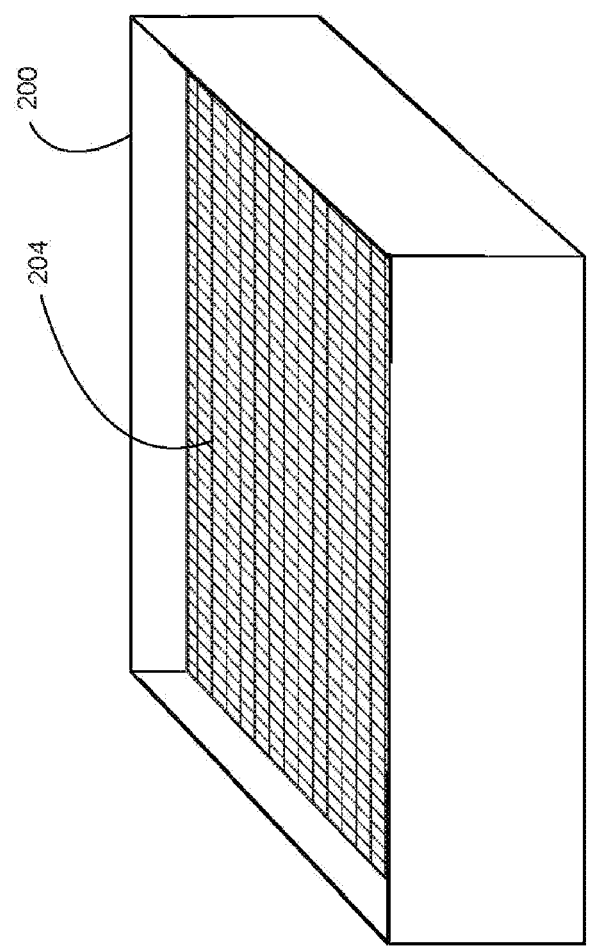
FIG. 5B illustrates the intermediate layer on an exposed surface of the nutritive vehicle in accordance with the preferred embodiment of the present invention.

Step 3—Application of intermediate layer—A top surface of the flattened nutritive vehicle 202 is covered by an intermediate layer 204 which is a permeable membrane. FIG. 5 illustrates the intermediate layer 204 placed on the top surface of the nutritive vehicle 202 in accordance with the preferred embodiment of the present invention.

In a preferred embodiment, a prepared intermediate layer is placed in the bottom of the empty enclosure, inoculated nutritive vehicle is packed on top of this layer and is flattened with pressure, filling up the enclosure to the proper depth and density. The enclosure is covered with a lid while the nutritive vehicle is given 2-4 days to grow together into a mass. Finally, the solidified fungal material is taken out of the enclosure, flipped over to reveal the intermediate layer now on the top surface, and re-placed into the enclosure, returning the lid and is left to grow.

In an alternate embodiment, the intermediate layer 204 is stretched on a frame to create a flat and tensioned surface. This tensioned fabric is placed against a rigid surface, and the nutritive vehicle is then packed against the fabric to create a flat nutritive vehicle surface closely mated to the intermediate layer. In this instance, the exposed framed intermediate layer may be revealed on the bottom of the enclosure. In another instance, the exposed intermediate layer may be revealed on the top of the enclosure.

Step 4—Applying composite material—In a preferred instance, the enclosure is placed in an environment conducive to growth, and fungal tissue grows through the intermediate layer after a few days. This growth is visible as a 'fuzzy' layer beginning to appear on the surface of the exposed intermediate layer. Once a visible layer of 'fuzzy' fungal material has uniformly established itself through and on top of the intermediate layer (~1-4 days), fibers and/or textile that have been pasteurized are placed on top of this growth above the intermediate layer. This is called a 'composite layer'. Cellulose-based materials [e.g. cotton or rayon] are often used as they are both biodegradable and a non-preferred food source for *Ganoderma*, meaning they maintain strength through the growth process in ways that lignin-bearing materials do not. Lignin is a preferred nutrient to this organism over cellulose. As the fungal material grows under specific environmental and physical controls, the filamentous fibers will grow through this composite, away from the colonized nutritive vehicle from which they have grown, and expanding further to grow another layer of hyphae. This behavior of strands of hyphae growing away from a nutritional source in an expansive and explorative manner is typical to many types of filamentous fungi, and is almost universally observed in saprophytic fungi.

Various forms of textiles may be used as composite materials. In particular, woven or knit cellulose-based materials (e.g. cotton) with heavily fulled surfaces are preferred. The woven or knit structures provide strength and the tousled fibers of the fulled surfaces anchor the fungal material to the textile, lowering the risk of delamination in the finished composite materials.

In an alternate method for applying the intermediate layer, a sheet of tightly woven fabric is pasteurized and layered on the top surface of the flattened nutritive vehicle 202, such that it is pressed or sealed using liquid to fabric and nutritive vehicle are brought as into contact as closely as possible. This is pressed so to further enhance flatness and evenness of the top plane of interaction on the flattened layer 202. The sides of the fabric are tucked along the edges of the box-like enclosure 200 to further assist in flattening the fabric.

In an alternate embodiment, any number of composites may be applied in any order or sequence, or between layers of fungal material, to create sophisticated and specific material qualities.

Figure 8:
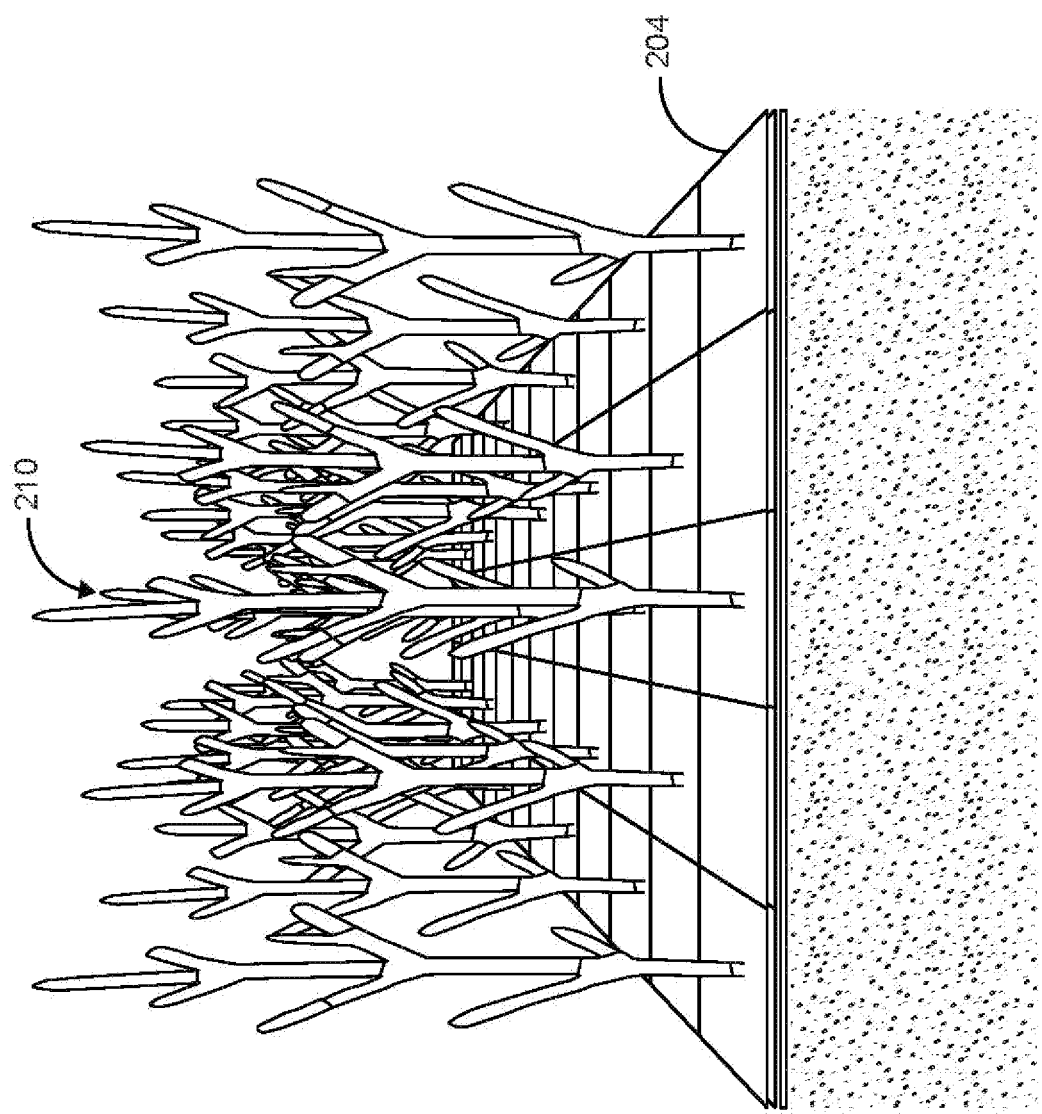
FIG. 8 illustrates a first dense network of hyphae growing off of the nutritive vehicle and through the intermediate layer in accordance with the preferred embodiment of the present invention.

The growing fungal tissue extends a dense network of hyphae 210 through openings of the intermediate layer 204 of the woven fabric up into the area above the intermediate layer 204 in an undifferentiated arbuscular mass, giving the appearance of fuzzy/fluffy white fibers. FIG. 8 illustrates the first dense network of hyphae 210 growing off of the nutritive vehicle 202 through the intermediate layer 204 in accordance with the preferred embodiment of the present invention.

After four days, the dense network of hyphae 210 forms into a live fungal tissue mat that has grown as an extrusion through the intermediate layer 204.

Step 5—Controlling environmental conditions—Growth environment is maintained such that mycelia tissue creation is maximized. A lid 206 is placed on top of the box-like enclosure 200 that is large enough to contain it from the larger environment within which it is embedded. This lid 206 preferably comprises a plurality of openings 208 and permeable aspects that allow for the transpiration of gases and humidity between the inside of the growing box-like enclosure 200 and the outside. FIG. 6 illustrates the enclosure lid 206 with the plurality of openings 208 in accordance with the preferred embodiment of the present invention.

In one embodiment, a piece of acrylic plastic or other non-reactive material measuring 38"×38", with the plurality of openings drilled every four inches in a grid array, is placed on the top of the box-like enclosure 200 and the growing nutritive vehicle 202.

Figure 7:
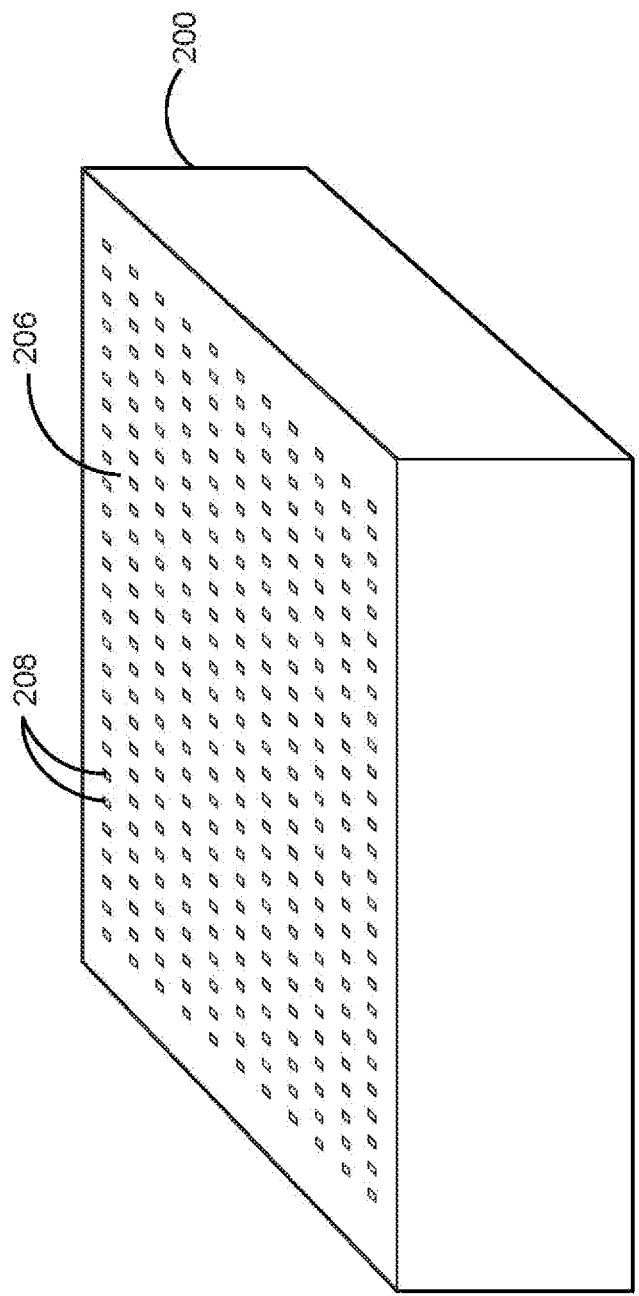
FIG. 7 illustrates the enclosure closed with the lid in accordance with the preferred embodiment of the present invention.

The growing box-like enclosure 200 of the covered nutritive vehicle 202 is closed with the lid 206 and kept in an environment that has controllable variables. FIG. 7 illustrates the enclosure 200 closed with the lid 206 in accordance with the preferred embodiment of the present invention. Proper atmospheric conditions inside the box include humidity ranging between 20-100% RH, rich in oxygen and a temperature between 50-95° F.

The room that the box-like enclosure 200 is growing within is preferably kept under positive pressure, ambient humidity levels at 10-15%, a temperature range of between 22-25° C., and total darkness. The materials are left to grow for a time period lasting at least two weeks with daily tending of the growing material, including manipulation of the growing fungal material.

Step 6—Manipulation of the growing fungal material—The growing hyphae are manipulated in such a way to depress them on top of the intermediate layer 204 through which they are growing, such that they are altered to be in contact with the surface 204.

Figure 9:
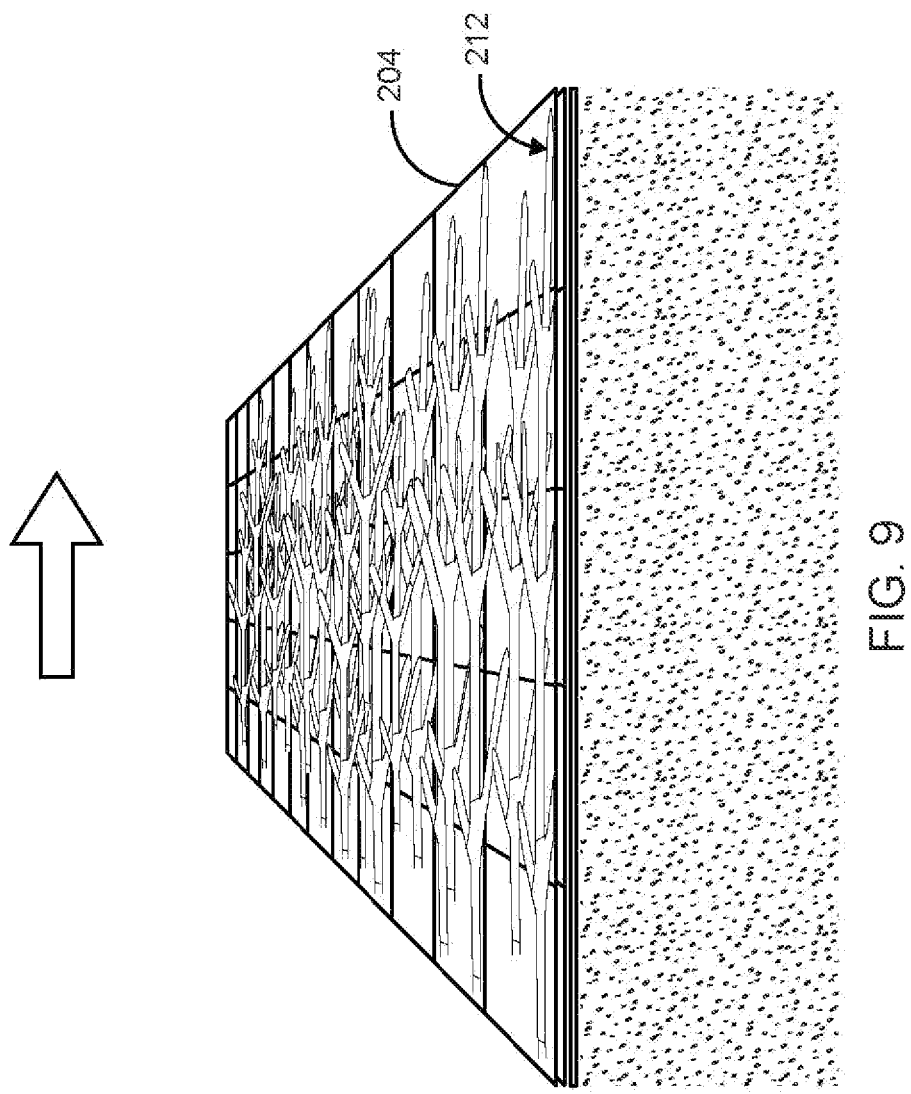
FIG. 9 illustrates the first dense network of hyphae shown in FIG. 8 being rolled flat in a first direction on an exposed surface of the intermediate layer to form a first flattened fungal material in accordance with the preferred embodiment of the present invention.
Figure 10:
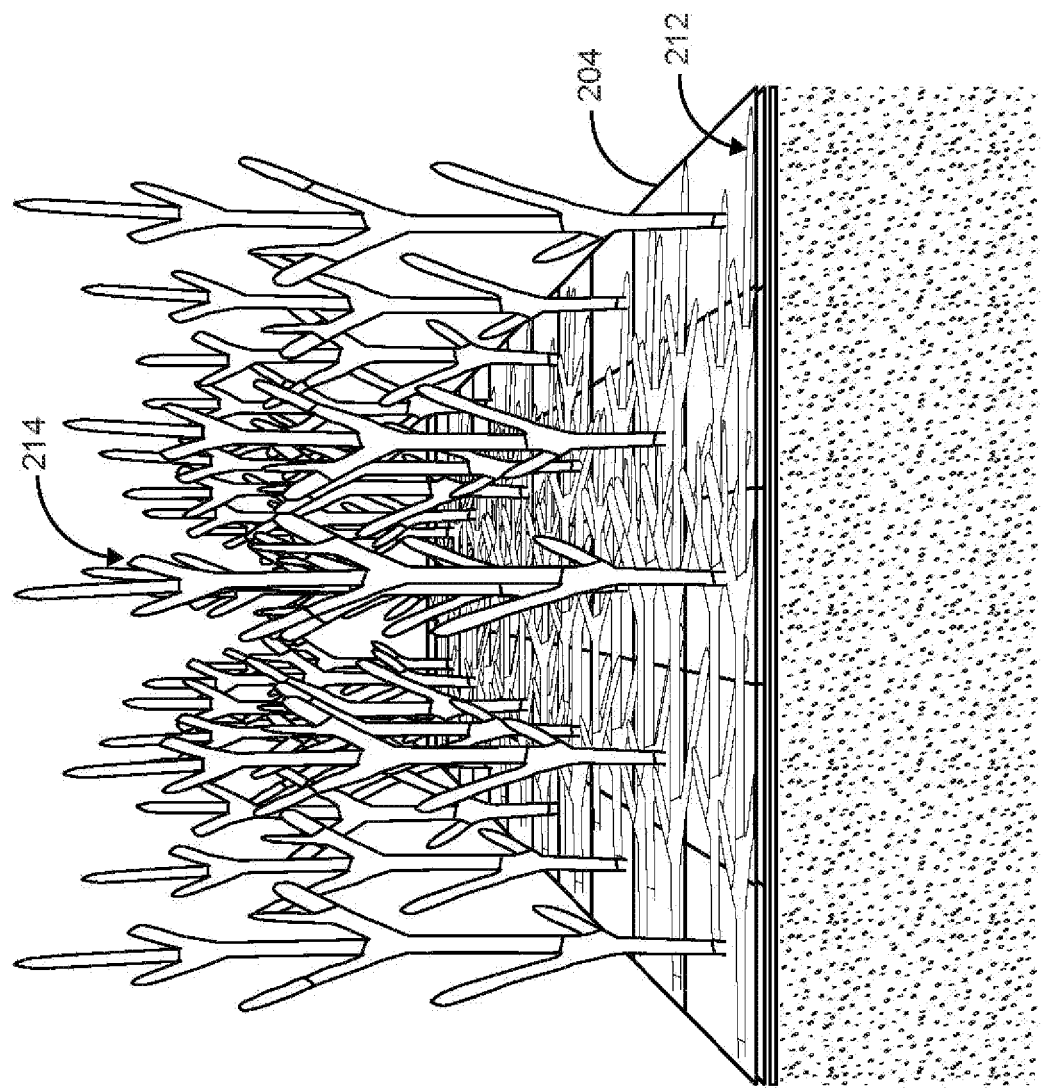
FIG. 10 illustrates a second dense network of hyphae regrown from the nutritive vehicle and through the intermediate layer and the first flattened fungal material shown in FIG. 9 in accordance with the preferred embodiment of the present invention.
Figure 11:
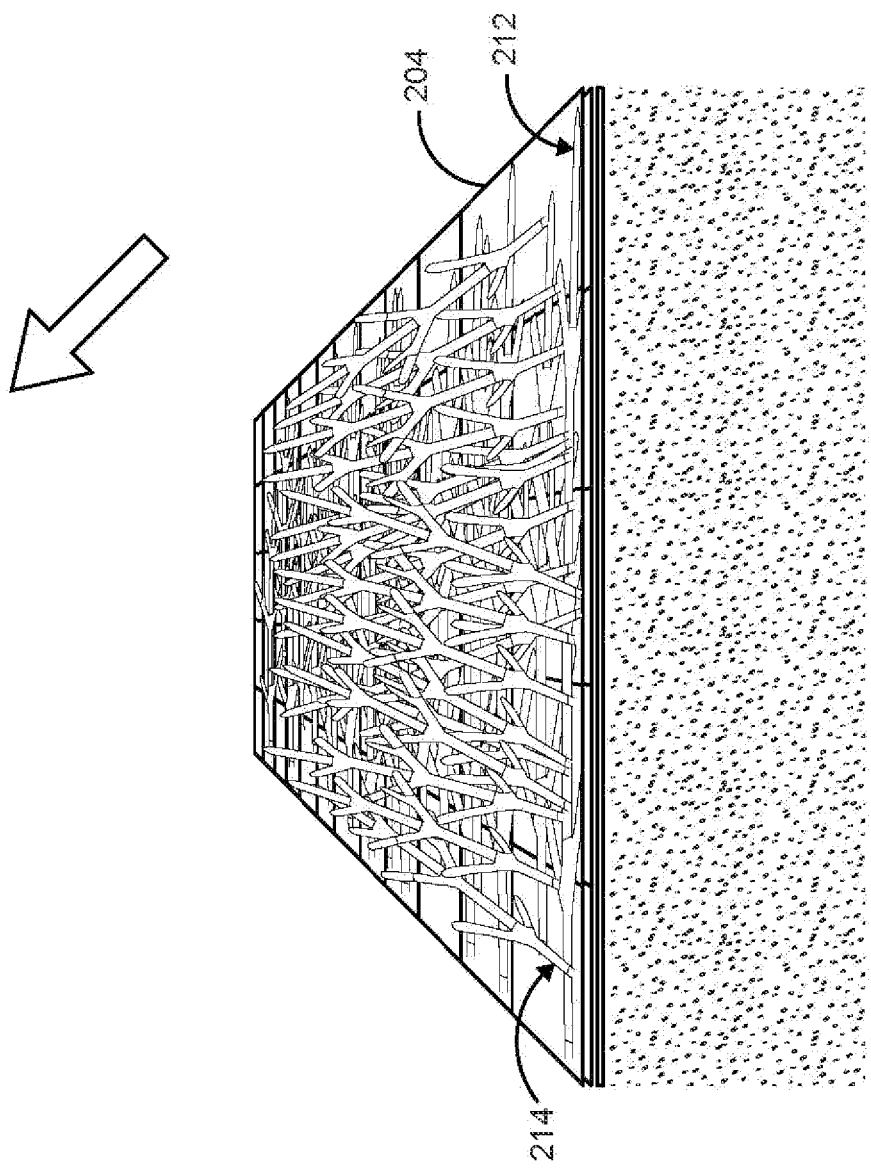
FIG. 11 illustrates the second dense network of regrown hyphae after being rolled in a second direction to form a second flattened fungal material in accordance with the preferred embodiment of the present invention.
Figure 12:
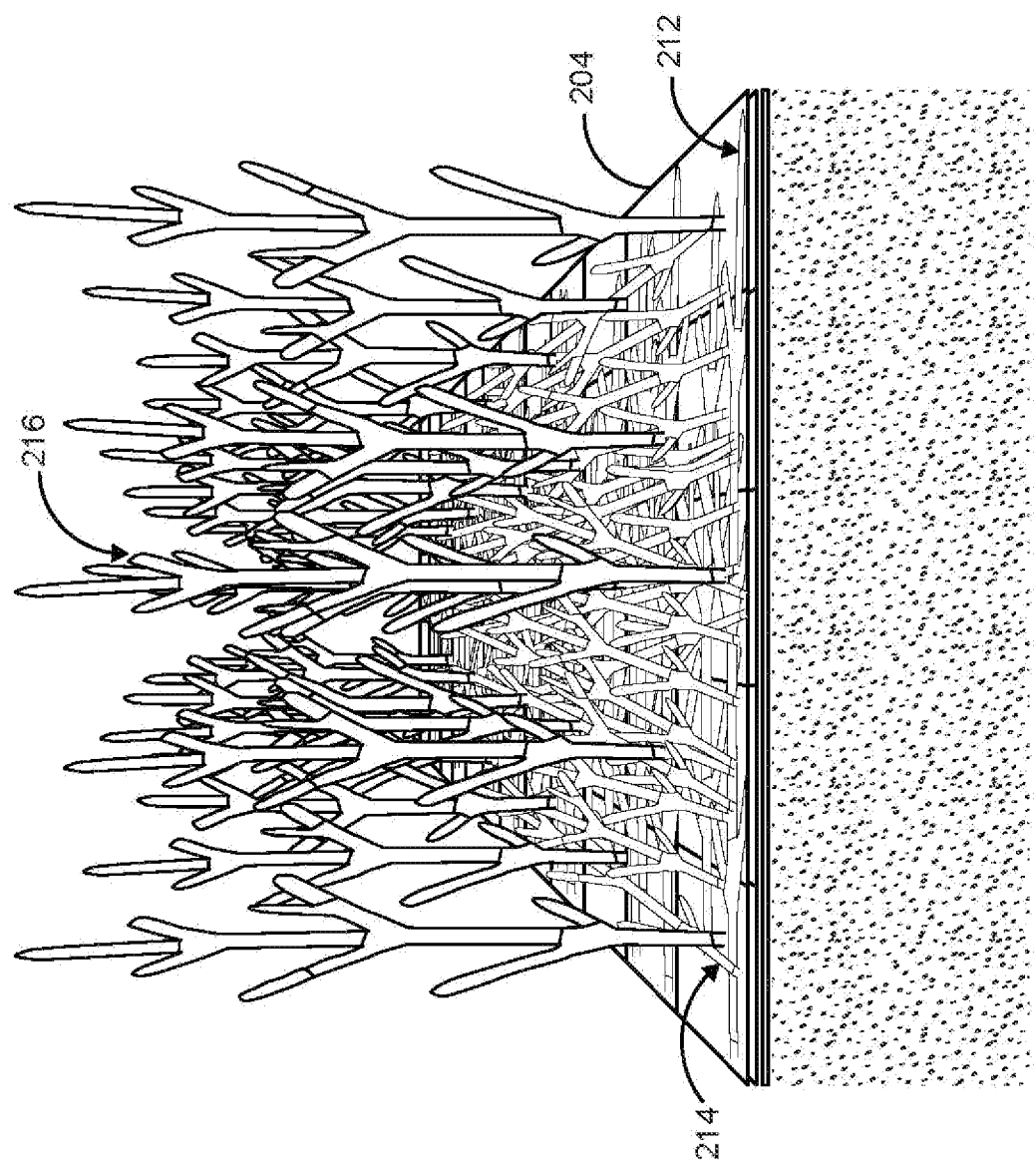
FIG. 12 illustrates a third dense network of hyphae regrown from the nutritive vehicle and through the intermediate layer and first and second flattened fungal materials shown in in FIG. 11 in accordance with the preferred embodiment of the present invention.
Figure 13B:
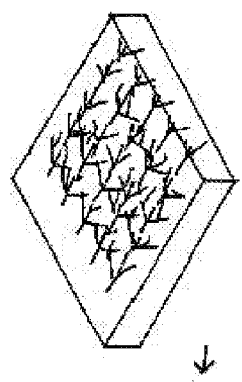
FIG. 13B is a perspective view of the hyphae being flattened in a first direction.
Figure 13A:
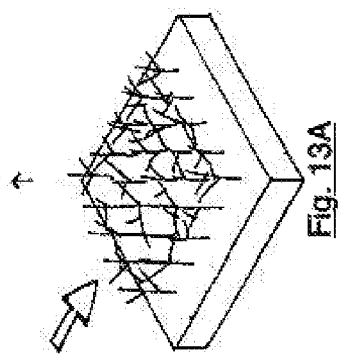
FIG. 13A is a perspective view of the hyphae in a growing state.
Figure 13C:
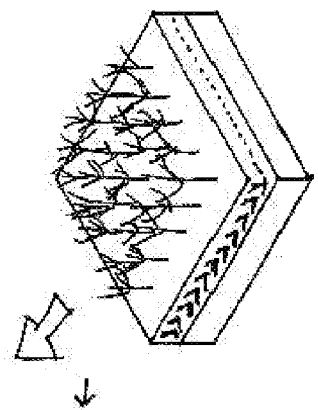
FIG. 13C is a perspective view of hyphae in a growing state.
Figure 13G:
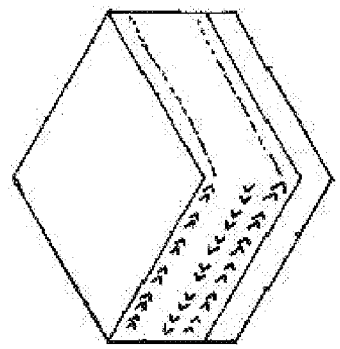
FIG. 13G is a perspective view of the hyphae flattened in multiple directions.
Figure 13D:
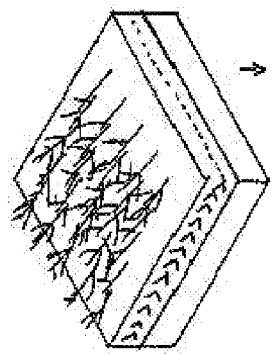
FIG. 13D is a perspective view of the hyphae being flattened in a second direction.
Figure 13E:
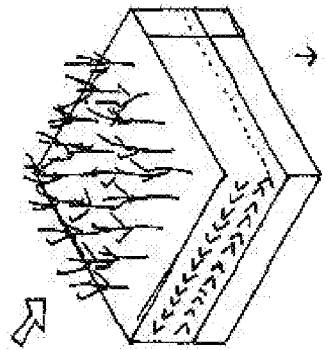
FIG. 13E is a perspective view of hyphae in a growing state.
Figure 13F:
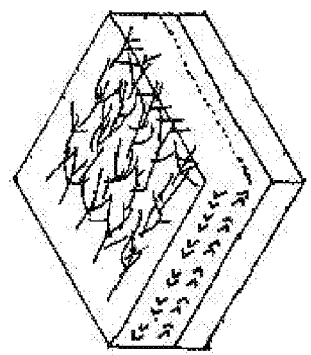
FIG. 13F is a perspective view of the hyphae being flattened in a third direction.
Figure 14D:
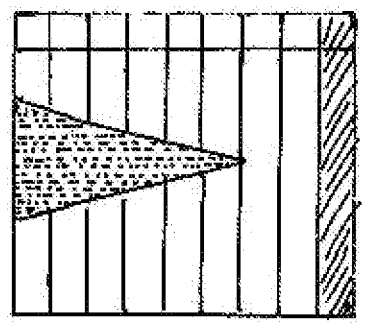
FIG. 14D is a fourth cross-sectional illustration of the fungal material after being pierced with a pointed element descending vertically therethrough.
Figure 14C:
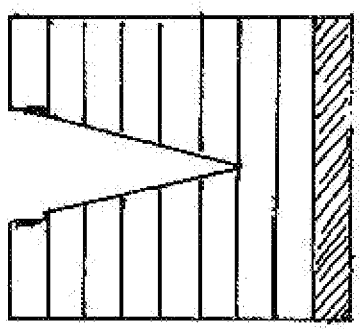
FIG. 14C is a third cross-sectional illustration of the fungal material being pierced with a pointed element descending vertically therethrough.
Figure 14B:
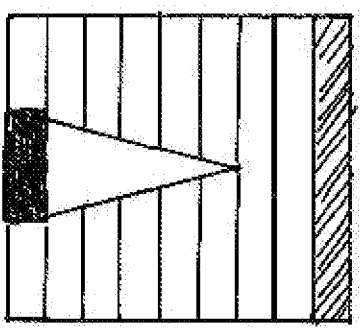
FIG. 14B is a second cross-sectional illustration of the fungal material being pierced with a pointed element descending vertically therethrough.
Figure 14A:
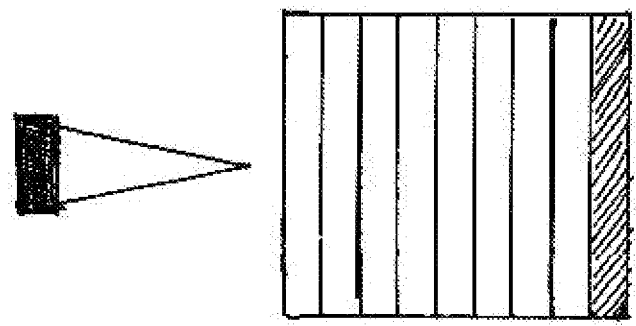
FIG. 14A is a first cross-sectional illustration of the fungal material about to be pierced with a pointed element descending vertically therethrough.

In a preferred instance a small rolling pin may be used to roll over a top surface of the intermediate layer 204 in a defined direction, thus altering the geometry of the growing plan of extending the fungal material. The entire surface of growing hyphae above the intermediate layer 204 is treated as such to achieve a uniform surface of flattened hyphae. FIG. 9 illustrates the first dense network of hyphae 210 shown in FIG. 8 being rolled flat in a first direction on the top surface of the intermediate layer 204 to form a first flattened fungal material structure 212 in accordance with the preferred embodiment of the present invention. FIG. 10 illustrates a second dense network of hyphae 214 regrown from the intermediate layer 204 having the first flattened fungal material structure 212 shown in FIG. 9 in accordance with the preferred embodiment of the present invention. FIG. 11 illustrates the second dense network of regrown hyphae 214 being rolled again in a second direction on the top surface of the intermediate layer 204 to form a second flattened fungal material structure 216 in accordance with the preferred embodiment of the present invention. FIG. 12 illustrates a third dense network of hyphae 218 regrown from the intermediate layer 204 having the second flattened hyphae 216 shown in FIG. 11 in accordance with the preferred embodiment of the present invention.

A formula comprising Tea Tree oil, soap and water is sprayed on top; however, combinations of those liquids or just one of those liquids may be used. This action is preferably repeated each day for the next ten days, with the direction of the roller alternating 90 degrees each day. By this method, conjoined layers of orthogonally-oriented hyphae are created.

In an alternate embodiment, multiple number of fungal material sheets and a multiple number of textiles may be stacked and incubated until these components compose a uniform solid. In between these layers, 'scoring' or 'scratching' the surfaces much like in traditional ceramics practices may increase the strength of the bond and improve the resistance to delamination between layers.

Environmental factors within the growing box-like enclosure 200 or the room that contain the box-like enclosure 200, may be altered so as to affect the growth characteristics of the fungi strain. Sprays, particles, fibers, and/or other additives and solutions may be added to the growing fungal mass. The layers might be scratched and otherwise altered to interweave/intermesh multiple growth layers or void spaces.

Step 7—Delamination of sheet—When the extruded fungal material structure has accreted to a desirable consistency and thickness, a sheet of fungal material structure is delaminated from the intermediate layer 204 and disassociated from the nutritive vehicle 202 from whence it originated.

A surgical knife or scissor may be used to cut through the growing surface, close to the sides of the box-like enclosure 200 in which the growing mass is contained. The sheet of fungal material structure is pulled up from a corner, much as one pulls a sticker off of its paper backing. In such a manner, the sheet of fungal tissue can be pulled off and retain its structure as an autonomous object in the form of a sheet.

In an alternate embodiment, the edge of the fungal material sheet extends over the enclosure such that no cutting is needed to separate the sheet of fungal material from the delamination layer.

Step 8—Post-growth processing of sheet—The material is soaked in a solution of catechol tannins equal in concentration to those used in animal leather processing. This strengthens the material through chemical tanning. In one embodiment, this is completed by soaking the material in a tannin solution of quebracho tree extract at boiling temperature for at least 4 hours.

The delaminated sheet can be treated with a plasticizing agent to impart flexibility when dry. It is soaked in a bath of 4:1 water-to-propylene glycol for 60 minutes, optionally pressed to remove excess liquid, and then hung to dry.

Once dry, the material is pressed at a temperature above 200 F between smooth heated plates at a pressure above 5 pounds per square foot for a time greater than 15 seconds. This compresses the material, imparts an even thickness, and gives a smooth surface texture. In an alternate embodiment, the plates used for pressing the material can be textured and used to impart a desired texture to the material.

The material can be dyed (for example by painting with an oil-based leather dye) and dried. It can then be coated in a finishing wax (composed for example of coconut oil, carnauba wax, and beeswax) and buffed.

The material can be treated with a water-resistance or waterproofing agent. For example, the material can be sprayed with any number of durable water repellant finishes such as Parylene C.

Example 2—A process for making a fungal tissue composite in accordance with certain embodiments of the invention includes.

Step A—Nutritive Vehicle Preparation
  A.1—mixing of nutrient components and water
  A.2—sterilization or other reduction of biotic load
  A.3—inoculation of nutritive vehicle with mushroom tissue
  A.4—mixing of all components
Step B—Vessel Preparation
  B.1—filling the vessel with the prepared nutritive vehicle
  B.2—leveling the surface of the nutritive vehicle
  B.3—preparation of intermediate layer B.4—placing a lid on the vessel with appropriate environmental controls Step C—incubation and growth of the fungal material C.1—growth of fungal hyphae through intermediate layer C.2—manipulation of hyphae as they are growing C.3—placement of fibers, mesh, or other materials on top of growing hyphae C.4—manipulation of hyphae as they are growing C.5—the environmental conditions may be altered to elicit desired growth behaviors C.6—various additives may be brought into the surface of the fungal tissue composite or into the environmentally administrated space so as to alter the morphology and character of the growing hyphae Step D—Delamination of the Fungus Tissue Material from the Nutritive Vehicle Step E—Manipulation and Growth E.1—compressing the fungal tissue composite to the desired dimensions and density E.2—bringing one part of the fungal tissue in contact with another part of the tissue E.3—bringing one part of the fungal tissue in contact with another tissue element E.4—forming the fungal tissue into a desired shape E.5—bringing one part of the fungal tissue in contact with another element E.6—let grow for 0-96 hours Step F—Additional Processing F.1—drying of the fungal tissue composite, for example by convection, conduction, microwave, freeze drying or other F.2—dried material is sanded, cut or milled to shape Step G—Post Processing G.1—adding a plasticizer or other post-growth processing steps Example 3

The following Example will provide various methods and techniques illustrated in FIG. 13-FIG. 19. This is a process through which hyphae from defined species of filamentous fungi are propagated from a colonizable nutritive vehicle that has been inoculated with said chosen fungi. Preferred species include the Ganodermas, the order Polyporales generally, and including all saprobic types of fungal candidates that derive sustenance from lignin and cellulose rich sources. The invention utilizes an intermediate membrane layer, located between the colonizable nutritive vehicle and the environment into which the fungal hyphal will grow. This intermediate layer can act as both a structural component as well as a means of manipulating the fungal tissue that grows through it, and is instrumental in the delamination and physical removal of the desired fungal tissue that has grown upon the colonizable nutritive vehicle.

The physical characteristics of growing fungal tissue are manipulated by direct and passive means. Direct means include intentional and specific changes through application of acute physical actions upon the nutritive vehicle such that its consistencies, orientations, and other physical aspects might be altered as is desired. These include mechanical, pneumatic, hydraulic and other actions that might be brought to bear upon said fungal tissue in such a manner as to cause consequential alteration of the fungal tissue. Other factors used to manipulate the characteristics of the growing fungal hyphae include: the application of both global and localized conditions through deposition of fluids, fibers, and other additives; control of optical conditions the growing fungal hyphae are subject to, and the selective application of heating and cooling elements. (e.g.: a heated roller or laser can be used to transform a selected area into a hardened or otherwise artifactual state of being). Passive means of altering the growing fungal tissue include the control of environmental climates and conditions of the entire fungal tissue or microclimates of regions of the growing fungal tissue.

In one instance, the nutritive vehicle is placed into a frame or container, the nutritive vehicle is colonized with fungal tissue expressing fungus of a desired type, the nutritive vehicle is uniformly distributed in a container and leveled to form a plane horizontal to the apical direction of the growth of fungal tissue above said plane. This plane is defined as the point of interaction or plane of interaction. Next, an intermediate solid or woven membrane, fabric or mesh is placed atop the plane of interaction so as to occupy the plane. Such a material can enable uniform growth.

Environmental conditions are maintained to a standard necessary for growth and extension of hyphae. Next, the fungal material is periodically manipulated to grow in particular and determined directions such that it can be arranged into orthogonal structures, lattices, or other layered organizational arrangements. In such a way, distinct layers can be induced to grow with determined states and structural formations within the body of the fungal tissue.

Once the desired thickness and organization is achieved, the fungal tissue is delaminated from the intermediate layer. The presence of the intermediate layer enables the fungal material to be cleanly removed without affecting the colonizable nutritive vehicle from which it permeated. The sheets or materials can be removed in such a way that the intermediate layer remains as a part of the generative base and a new skin of fungal tissue can once again grow through it in a permeable manner. The fungal material is then processed to product specifications.

In Detail

1. This disclosure requires a volume of nutritive vehicle that is colonized with a chosen of fungus of interest that has the habit or ability to generate fungal tissue within said instance as is desired. Not all fungus will express fungal tissue in the manner necessary for the invention, and certain organisms function better than others.
2. In one instance, a container may be used to hold the inoculated nutritive vehicle. The material does not have to be fully colonized before entering the container in which it will be housed, but at some point, the material may be fully colonized to properly express tissue as is desired. In the instance that an even and uniform product is desired, the boundary with the greater environment from which the tissue is desired to be expressed is flattened, and the nutritive vehicle is loaded in an even way such that there is homogeneous distribution within its planar form. Alternative instances utilize non-planar surfaces of nutritive vehicle, heterogeneous distribution of nutritive vehicle or combinations of these techniques.
3. At a certain point in time, after the nutritive vehicle has been inoculated, an intermediate layer, distinct from the inoculating nutritive vehicle, is placed atop the nutritive vehicle. In one instance, the intermediate layer is a flat surface. In one instance, this flat surface is a piece of woven fabric laid atop the nutritive vehicle, such that the two materials are immediately adjacent, or such that the fabric is embedded and the nutritive vehicle and fabric occupy the same plane. Alternatively, other membranes, sheets, meshes, pellicles and tissues can be used as an intermediate layer.
4. In one embodiment, the intermediate material is a fabric of a consistency that will not permanently bind to the fungal material, (that is, it will only allow fungal tissue to pass through the fabric without degradative or incorporating agencies altering it such that it is difficult to remove the fungal tissue that has grown upon said fabric). This fabric as an intermediate layer allows one to separate the fungal material from the nutritive vehicle without additional processes, and frees the nutritive vehicle to be reused for the growth of further fungal tissues. Without the use of an intermediate material, the fungal material will unevenly generate, bind, and fuse to the heterogeneously ordered fibers that constitute the nutritive vehicle, leading to a disrupted surface of the nutritive vehicle, and unevenness in the growing sheet of fungal tissue. In this embodiment of the invention, the presence of a uniform and flat intermediate material atop of nutritive vehicle enables a consistent surface for the fungal material to grow from, and upon which to be further manipulated. Another embodiment of this invention can be achieved without any fabric, membrane, or substantive intermediate layer. An intermediate layer can be created on top of the colonized nutritive vehicle through heat or chemical polymerization of the cellulose, chitin or other materials that constitute the nutritive vehicle or fungal tissue/
   a. Spray on sealers, chemicals and other liquids can also be used to create a non-woven, permeable, or solid intermediate layer between the colonized nutritive vehicle and the fungal tissue that will be generated from said colonized nutritive vehicle.
5. The remaining nutritive vehicle may then be used again to grow new expressions of fungal tissue. Another instance involves the reapplication of the delaminated fungal material onto the same nutritive vehicle from which it had been removed, but in a different orientation or formation. Another instance involves the reapplication of the delaminated fungal material onto a nutritive vehicle inoculated with a different type of fungus.
6. Direct electrical stimulation and actuation of intermediate layer.
   a. In one embodiment of the invention, the intermediate layer consists of system that allows for electric current to be applied to specific X and Y coordinates, such that precise and determined electrical current might be applied to a desired location of said intermediate layer. Localizable electrical stimulation is used to change composition and growth habits of hyphae, for example increasing the frequency of hyphal fusion and branching.
   b. In another embodiment, an electric current in continuous or discontinuous form is applied to charge the entire surface in a gross manner.
   c. In another instance, an electric current is directed toward the actuation of characteristics of the intermediate layer, such that a permeable membrane might alter its surface qualities to open or close pores, or otherwise alter its surface from said electrical stimulation to actuate a field, mechanisms, or artifacts, or otherwise have an effect on the growth and characteristics of the growing fungal tissue.
7. Surface deposition, application, alteration
   a. Different types of additives can be incorporated into the growing fungal tissue through application or deposition. In one embodiment, cellulose and other organic fibers of preferred lengths, flocculation, and other structural characteristics are deposited on the top of the surface plane of the growing fungal tissue such that said fibers are all oriented along a preferred axis or other orientation. These deposited fibers are interspersed in an ordered manner as is desired across the surface of said fungal tissue. These fibers can be used as guides and scaffolds for the orientation of the fungal tissue, both to promote or inhibit growth of the tissue in preferred ways. These fibers enable the engineering of macro and micro qualities of the fungal tissue including strength, shear, elasticity, and memory. Alternatively, other types of fibers, and organization of said fibers can be used.
   b. Particles can be dispensed and otherwise broadcast and impressed upon the surface of said growing fungal tissue. Through deliberate and successful application of said particles, and subsequent engulfment within said fungal tissue, the placement of particles can be determined within a three-dimensional matrix.
   c. Water, liquid solutions, gels and other viscous agents can be deposited on the growing surface of the fungal tissue in determined volumes, patterns and distributions. These viscous agents affect localized conditions by making available resources that can encourage or inhibit qualities of growth and extension of fungal hyphae. Through this deposition of viscous agents, localized and emergent tissue development can be affected with determination and fidelity. Hydrostatic charges on said deposited viscous agents also have influence over the behavior and direction of apically extending hyphae above the tissue surface.
   d. In another instance, a layer of nylon textile or other materials are impressed into the surface of a fungal material, and on top of this is placed another fungal material. Over time, the fungal materials will fuse together, embedding the composite material within.
8. In the most generic term, an inoculated nutritive vehicle for a given fungus will naturally differentiate towards the generation of sexual organs if left unregulated. In a preferred method, the hyphae growing above the intermediate layer are manipulated, stressed, or otherwise altered and depressed or otherwise made to come in contact with the surface from which they had originally extended. If treated in such a way the fungal material will be withheld from differentiating into organs of sexual reproduction, and instead will return to a searching and extending manner above the surface from which it is growing. A process of stress, alteration, and stimulation can be repeated indefinitely to repress the fungal organism from establishing sporulating or otherwise desirable tissues.
   a. Next, it is necessary to create the conditions that optimize arbuscular expression. In one instance, a permeable intermediate layer ensures uniformity in fungal tissue expression as it permeates through said intermediate layer. From here on, mycelial growth is manipulated via external manipulation and signals, and the fungal tissue's internal expressions and signals.
   b. Without proper control, fungal tissue will differentiate into tissues that will become organs of sexual reproduction and sporulation. In the instance that an undifferentiated product is desired, environmental conditions serve as a primary agent by which organismal development might be determined and directed. In the instance that intentional inconsistencies are desired in the product, disturbances across the plane of growth can be induced through environmental controls. In one instance, the relative presence of O2 and CO2 can be used to determine desired growth habits. In another instance, control of temperature can be used to similar effect. In another instance, aspirated air that is introduced to the growing environment can be used to prevent or promote development of the growing fungal organism. Other internal aspects of the colonized nutritive vehicle might be intentionally organized to direct the growth of the organism, including distribution and availability of nutrients within the nutritive vehicle, intentional use of antibiotics for masking, physical amendments and additives that might also inhibit and/or promote various forms of growth. Other tropic responses of the organism (gravitropism, phototropism, etc.) can be used to direct growth, both through immediate control of the growing environment, or by design and organization of said environmental conditions.

9. Alteration of the surface of the growing mycelial mass is primary to engineering fungal tissue development and constitution.

Referring next to FIG. 13A-13G, in a preferred embodiment, the hyphae might be flattened with a roller in one direction, as the roller cross from point A to point B. In doing so, the roller flattens the hyphae back onto the plane from which they grew. As the hyphae re-grow vertically, a roller can now pass from point B to point A, again flattening the vertically growing hyphae. This method can be employed to weave the body of fungal material into novel patterns that are deliberately synthetic in organization of the orientation and connections of the hyphae that constitute its said fungal tissue.

1. Growth of arbuscular hypha above plane of fungal tissue
2. Fungal material flattened in a determined direction
3. Regrowth of arbuscular hypha above plane of fungal tissue
4. Fungal material flattened in a determined direction
5. Regrowth of arbuscular hypha above plane of fungal tissue
6. Fungal material flattened in a determined direction
7. Cross section showing alternatively oriented directions of fungal tissue in a determined pattern.

Turning to FIG. 14A-D, in a preferred embodiment, the fungal tissue might be pierced or otherwise displaced with a pointed element descending vertically through said fungal tissue. After the element has been depressed into said fungal tissue and removed, a void space is created as a result. Subsequent regrowth of fungal material fills in void spaces, resulting from pointed element, and creating vertical connection plugs between vertical aspects of said tissue (said volumetric space can also be filled with a secondary material/amendment/additive, other fungal species, other organisms)

1. Cross section of fungal tissue with pointed element that will be depressed vertically into said fungal tissue.
2. Pointed element depressed within fungal tissue
3. Pointed element removed from fungal tissue, leaving a void space created as a result.
4. Subsequent regrowth of fungal material, which fills in void space resulting from pointed element, and creating vertical connection plugs between vertical aspects of said tissue (said volumetric space can also be filled with a secondary material/amendment/additive, other fungal species, other organisms)

Turning next to FIG. 15A-G, this method can be employed to grow the fungal material into novel patterns that are deliberately synthetic in the organization of their tissues through their structural constitution. Vertical and horizontal aspects of said tissue can be propagated in such a manner to intentionally connect, weave, and otherwise engineer successive layers of chronologically emergent mycelial growth.

1. Cross section of fungal tissue, with pointed elements that will be depressed vertically into said fungal tissue.
2. Pointed elements depressed within fungal tissue
3. Pointed elements removed from fungal tissue, leaving void space created as a result.
4. Subsequent regrowth of fungal material, filling in void spaces from pointed elements, and creating vertical connection plugs between vertical aspects of said tissue (said volumetric space can also be filled with a secondary material/amendment/additive, other fungal species, other organisms)
5. Subsequent repeat of actions in offset manner.
6. Orthogonal view of a section of fungal tissue treated as such in a repeated manner, showing how patterned X Y Z configurations of vertical and horizontal aspect so said tissue might be determinatively organized.

Turning next to FIG. 16A-K, in a preferred embodiment, the sheet of fungal tissue can be agitated by a bristled roller or other device, mechanism, or other agency that displaces and shreds the top surface of said tissue as it moves across its surface from one direction to another, to create a surface with an uneven manner. Said disturbed tissue regrows, is depressed or otherwise levelled into a form as is desired, with repeated agitation, regrowth, and depression. Interconnecting patterns of growth between chronologically developing tissues can be determined through said methods.

1. Cross section of fungal tissue, showing distinct growth of tissue in vertical manner.
2. Toothed comb or other element raked across the top surface of fungal tissue
3. Shredded and otherwise agitated surface after passage of toothed comb
4. Regrowth of tissue with infilling fungal material (said volumetric space can also be filled with a secondary material/amendment/additive, other fungal species, other organisms)
5. Compression of arbuscular hypha so as to form uniform top surface.
6. Regrowth of top surface into distinct layers
7. Repeat: Toothed comb or other element raked across the top surface of fungal tissue.
8. Repeat: Shredded and otherwise agitated surface after passage of toothed comb.
9. Repeat: Regrowth of tissue with infilling fungal material of said tissue (said volumetric space can also be filled with a secondary material/amendment/additive, other fungal species, other organisms)
10. Repeat: Compression of arbuscular hypha so as to form uniform top surface.
11. Cross section of fungal tissue after repeated cycles of agitation and regrowth, showing heterogeneous intermixing and regrowth of adjacent areas within the material.

As shown in FIG. 17A-J, the fungal tissue may be altered with an element that will displace said fungal material as it moves in a transverse manner across it, creating contiguous elements, pits, channels, lattices and other alterations of said tissue as a result. Said altered tissue regrows to connect or fill said displaced aspects of the transversed surface of said fungal tissue. Interconnecting patterns of growth between chronologically developing tissues can be determined through said methods. Woven tissues and otherwise conjoined reinforcements of fungal tissue can be determined in such manner.

1. Cross section of fungal tissue, showing distinct layers, with sharpened element that will displace said fungal material as it moves in a transverse manner across it.
2. Sharpened element dislodging and altering said fungal tissue.

Two alternative options are presented

1. Fungal tissue after passage and interaction with sharpened element, demonstrating displaced but still contiguous aspects of said fungal tissue altered in relation to the greater fungal mass upon which it is in contact. In another instance of this step a roller may be moved across the top of the fungal tissue in a transverse manner so as to impress one aspect of the organism in greater proximal contact with other aspects of itself. Over time the fungal distinct aspects of the greater fungal tissue will bind and form into a contiguous whole.
2. Fungal tissue after passage of sharpened element from one direction to another, demonstrating extraction of channel like displacement of said fungal tissue.
   i. Regrowth of tissue into channel void space with infilling fungal material (said volumetric space can also be filled with a secondary material/amendment/additive, other fungal species, other organisms)
   ii. Sharpened elements dislodging and altering said fungal tissue from another direction.
   iii. Fungal tissue after passage of sharpened element from one direction to another, demonstrating extraction of channel like displacement of said fungal tissue.
   iv. Orthogonal view of a section of fungal tissue treated as such in a repeated manner, showing how with patterned X Y Z configurations of vertical and horizontal aspect said tissue might be purposefully organized.

As shown in the preferred embodiment of FIG. 18A-D, the surface plane of the growing fungal tissue is embedded with discrete fibrous elements during its manufacture such that said fibers are all oriented along a preferred axis or other orientation. These deposited fibers can be used as guides or scaffolds for the orientation of the fungal material, both to promote or inhibit growth in preferred ways. These fibers enable the engineering of macro and micro qualities of the fungal tissue, including strength, shear, elasticity, chirality of deformation, and memory. Alternatively, other types of fibers, and organization of said fibers can be used.

In an alternative embodiment (not shown), a discrete fibrous filament is placed upon growing fungal tissue in a preferred geometric orientation. Then, a layer of discrete filaments is placed to form a preferred orientation. Next, additional mycelial growth encapsulates the fibrous filaments, after which a new layer of filaments is added in a differing geometric orientation from the previous filament layer. Finally, another layer of filaments is placed upon the fungal tissue. Subsequent growth occurs from steps 2 onward, until completion.

As shown in FIG. 19A-D, particles may be dispensed and otherwise broadcast and impressed upon the surface of said growing fungal tissue. Through deliberate and successful application of said particles, and subsequent engulfment within said fungal tissue, the placement of particles can be determined within a three-dimensional matrix.

In an alternative embodiment (not shown), a particle is dispensed and impressed upon growing fungal tissue, a layer of discrete particles is embedded in their particular geometric orientation, and growth proceeds. Next, additional mycelial growth engulfs the discrete particles, thus incorporating them into the structure, after which a new layer of particles is added. Finally, the new layer is embedded in a differing geometric orientation from the previous layer, creating a three-dimensional matrix of particles within the fungal tissue. The steps herein may be repeated.

Thus, although the invention has been described with respect to specific embodiments, it will be appreciated that the invention is intended to cover all modifications and equivalents within the scope of the following claims.

The invention claimed is:

1. A system for growing fungi, the system comprising:
   a. a nutrient substrate including a mixture of discrete particles and nutrients capable of providing nutritional resources for the growth of a fungal inoculum in an enclosure;
   b. a porous material defining an intermediate layer being placed on the top surface of the nutrient substrate within the enclosure, which does not readily bind fungal material, and stimulates the growth of the fungal inoculum, wherein the porous material is micro-perforated or woven, and is selected from the group consisting of metal, polymer, and ceramic plate;
   c. an administrable space positioned away from said nutrient substrate in which fungal tissue extends by means of a successive fungal material layer, the successive fungal material layer within said administrable space includes fungal hyphae;
   d. a first fungal material layer of fungal tissue connecting said nutrient substrate to said administrable space;
   e. a growth field comprising growth field locations such that growth of said first layer of fungal tissue is directed through said growth field locations so as to create said successive layer of fungal tissue; and
   f. a first portion of fungal material delaminated from said first fungal material layer; whereby the growth of the fungal inoculum into a dense network of hyphae allows the hyphae to produce the fungal material on the nutritive vehicle and the intermediate layer.

2. The system for growing fungi of claim 1, wherein the fungal hyphae in the successive layer are fused with at least one additional fungal hyphae.

3. A system for growing fungi, the system comprising:
   a. a nutrient substrate capable of providing nutritional resources for the growth of a fungal inoculum in an enclosure, the fungal inoculum growing from said nutrient substrate into fungal tissue, the fungal tissue comprising fungal hyphae;
   b. a porous material defining an intermediate layer being placed on the top surface of the nutrient substrate within the enclosure through which fungal material extends and stimulates the growth of the fungal inoculum, wherein the porous material is micro-perforated or woven, does not readily bind the fungal material, and is selected from the group consisting of metal, polymer, and ceramic plate;
   c. an enclosed administrable space positioned away from said nutrient substrate in which said fungal tissue extends by means of a successive fungal material layer;

d. a growth field comprising growth field locations such that growth of a first layer of fungal tissue is directed through said growth field locations so as to create said successive layer of fungal tissue material; and e. a first portion of the fungal tissue in contact with a second portion of the fungal tissue, wherein said fungal hyphae are distorted such that at least one individual hypha comes into contact with at least one additional fungal hypha; whereby the intermediate layer prevents the fungal material from permanently adhering to the nutrient substrate and prevents damaging or tearing of the nutrient substrate when removing the fungal material.

4. The system for growing fungi of claim 3, wherein said fungal tissue is joined to the first fungal material layer and the successive fungal material layer.

5. The system for growing fungi of claim 3, wherein said fungal hyphae are fused to one another.

6. The system for growing fungi of claim 3, wherein said intermediate layer provides uniform initial conditions of growth, thereby achieving uniform growth pattern of the fungal tissue and directing said growth pattern into a definable plane.

\* \* \* \* \*